(12) United States Patent
Tajima et al.

(10) Patent No.: US 7,947,512 B2
(45) Date of Patent: May 24, 2011

(54) DISPENSING CYLINDER, LARGE CAPACITY DISPENSING DEVICE, AND METHOD OF USING LARGE CAPACITY DISPENSING DEVICE

(75) Inventors: Hideji Tajima, Maisudo (JP); Yoshinao Hirahara, Maisudo (JP)

(73) Assignee: Universal Bio Research Co., Ltd., Matsudo-shi, Chiba (JP)

( * ) Notice: Subject to any disclaimer, the term of this patent is extended or adjusted under 35 U.S.C. 154(b) by 1242 days.

(21) Appl. No.: 10/552,913

(22) PCT Filed: Apr. 15, 2004

(86) PCT No.: PCT/JP2004/005385
§ 371 (c)(1), (2), (4) Date: Aug. 1, 2006

(87) PCT Pub. No.: WO2004/092710
PCT Pub. Date: Oct. 28, 2004

(65) Prior Publication Data
US 2006/0263260 A1    Nov. 23, 2006

(30) Foreign Application Priority Data
Apr. 15, 2003    (JP) .................................. 2003-109838

(51) Int. Cl.
*B01L 3/02* (2006.01)
(52) U.S. Cl. .................. 436/180; 73/864.13; 73/864.14; 73/864.16; 73/864.17; 422/501; 436/526
(58) Field of Classification Search .................. 422/100; 73/864.01–864.25; 436/526, 180
See application file for complete search history.

(56) References Cited

U.S. PATENT DOCUMENTS

| | | | | |
|---|---|---|---|---|
| 3,754,863 A * | 8/1973 | Reunanen | ....................... | 436/54 |
| 4,602,517 A * | 7/1986 | Schultz | ...................... | 73/864.16 |
| 5,275,951 A * | 1/1994 | Chow et al. | ..................... | 436/50 |
| 5,309,959 A * | 5/1994 | Shaw et al. | ................... | 141/130 |
| 5,702,950 A | 12/1997 | Tajima | | |

(Continued)

FOREIGN PATENT DOCUMENTS

JP    60-21434 A    2/1985

(Continued)

OTHER PUBLICATIONS

Japanese Patent Office, "International Search Report," PCT/JP2004/005385, Jun. 1, 2004 (4pages).

*Primary Examiner* — Jan M Ludlow
(74) *Attorney, Agent, or Firm* — Haynes and Boone, LLP

(57) ABSTRACT

The invention relates to a dispensing cylinder, a large capacity dispensing device, and a method of using a large capacity dispensing device, and aims at providing a dispensing cylinder, a large capacity dispensing device, and a method of using a large capacity dispensing device, with high quantitativity and capable of suppressing the scale of the device and efficiently utilizing working space, despite the relatively large volumes of fluid handled. The construction comprises: a small diameter section, a large diameter section which communicates with the small diameter section and is capable of holding fluids, a sliding section provided in a slidable manner within the large diameter section which enables fluid to be sucked and discharged to and from the large diameter section through the small diameter section, and a connection section which connects the sliding section in a detachable manner to a suction and discharge mechanism which drives the sliding section.

28 Claims, 12 Drawing Sheets

U.S. PATENT DOCUMENTS

| | | | |
|---|---|---|---|
| 5,895,631 A | 4/1999 | Tajima | |
| 6,509,193 B1 | 1/2003 | Tajima | |
| 6,691,748 B1 * | 2/2004 | Tajima | 141/130 |
| 6,846,680 B2 * | 1/2005 | Friswell et al. | 436/180 |
| 6,869,571 B2 * | 3/2005 | Ingenhoven et al. | 422/100 |
| 2003/0026732 A1 * | 2/2003 | Gordon et al. | 422/63 |

FOREIGN PATENT DOCUMENTS

| | | |
|---|---|---|
| JP | 2-218961 A | 8/1990 |
| JP | 04-051647 Y2 | 4/1992 |
| JP | 7-83938 A | 3/1995 |
| JP | 3115501 | 3/1996 |
| JP | 11-160327 A | 6/1999 |
| JP | 2004-061397 A | 2/2004 |
| WO | WO/96/29602 | 9/1996 |
| WO | WO/97/44671 | 11/1997 |
| WO | WO 97/44671 A | 11/1997 |
| WO | WO 00/42410 A | 7/2000 |
| WO | WO01/53839 * | 7/2001 |
| WO | WO 02-063300 A | 8/2002 |

* cited by examiner

US 7,947,512 B2

DISPENSING CYLINDER, LARGE CAPACITY DISPENSING DEVICE, AND METHOD OF USING LARGE CAPACITY DISPENSING DEVICE

CROSS REFERENCE

This application is a United States national phase application of international patent application number PCT/JP2004/005385, filed Apr. 15, 2004, which claims priority to Japanese patent application number 2003-109838, filed Apr. 15, 2003, which priority is claimed.

TECHNICAL FIELD

The present invention relates to a dispensing cylinder, a large capacity dispensing device, and a method of using a large capacity dispensing device, and relates specifically to a dispensing cylinder, a large capacity dispensing device, and a method of using a large capacity dispensing device capable of handling relatively large volumes of fluid (approximately milliliters or greater).

The present invention is of use in fields where testing or processing is performed which requires relatively large volumes of fluid to be handled with high quantitativity and precision. The present invention is of particular advantage in fields which require testing, extraction, concentration, analysis and assays relating to genetic material such as DNA, RNA, mRNA and plasmids and biological material such as proteins, amino acids, and sugar chains, including engineering, foodstuffs, agriculture, fishery, pharmacy, sanitation, medicine, or scientific fields such as chemistry and biology.

The present invention is of particular advantage for example in the testing of large volumes of blood extracted by a vacuum blood tube, or the extraction or concentration of DNA from such blood, the extraction or concentration of DNA from organisms such as humans, or the extraction or concentration of DNA and the like, bacteria, viruses, and proteins and the like from foodstuffs (such as beverages, solids, meat, vegetables).

BACKGROUND ART

In one example of a conventional dispensing device, processing is performed collectively using a plurality of specimens and reagents each with a relatively small volume (from several hundred microliters to several thousand microliters) (Japanese Patent No. 3,115,501, International Patent Publication No. WO96/29602, International Patent Publication No. WO97/44671). This dispensing device handles relatively small volumes of fluid by fitting a plurality of pipette tips having the capacity mentioned, to a plurality of nozzles, and laying out not only a large number of containers with this capacity, but also a large number of unused and used pipette tips, and repeating an automatic process of fitting and detaching the pipette tips to and from the nozzles. In this dispensing device, so that suction and discharge can be performed by adjusting the pressure inside the pipette tip, the construction of the pipette tip is made simple by fitting the pipette tip to a nozzle which connects to a separate cylinder equipped with a plunger.

Thus, when handling relatively small volumes of fluid, even when the attachment and removal of pipette tips is repeated with not only a large number of pipette tips but also a large number of containers laid out, because the capacity of each pipette tip and each container is relatively small, a great deal of working space is not required. Furthermore, even when the pipette tips and cylinders are provided separately, they do not take up a large area.

Incidentally, when attempting to handle relatively large volumes of fluid greater than several tens of milliliters when there is a large number of inspection articles such as specimens to be tested, if a dispensing device is used which handles small volumes of fluid as described above, the processing cannot be performed all at once, and the fluid must be handled in smaller units. As a result, dispensing must be repeated a large number of times which is cumbersome. Furthermore, there is a problem in that for the sake of automation, a large number of used and unused pipette tips, as well as a large number of small capacity containers must be laid out, which may necessitate a large working space.

On the other hand, when a pipette tip with a large capacity is fitted to a nozzle, the volume of air used to adjust the pressure can be as much as the total of the capacity of the pipette tip, the capacity of the nozzle, and the capacity of the tube that connects to the separate cylinder. Taking into consideration that the volume of gases such as air is more variable to pressure and temperature than fluids, a problem occurs in that the increase in the amount of air to be handled due to the increase in capacity of the pipette tip causes a deterioration in the accuracy of the suction and discharge operations. Furthermore, it is necessary to provide not only a large capacity pipette tip but also a separate similarly large capacity cylinder for adjusting the pressure within the pipette tip, as well as a large number of large capacity containers to be used, and if the processing is to be automated, unused and used large capacity pipette tips in an detachable manner. Therefore there is a problem in that a vast working space may be required.

To solve the above problems, a first object of the present invention is to provide a dispensing cylinder, a large capacity dispensing device, and a method of using a large capacity dispensing device, which can perform processing with excellent quantitativity and high reliability despite handling relatively large volumes of fluids (greater than several milliliters, for example several ten to several hundred milliliters) for a large variety of inspection articles.

A second object is to provide a dispensing cylinder, a large capacity dispensing device, and a method of using a large capacity dispensing device, capable of suppressing the scale of the device and efficiently utilizing working space despite the large volumes of fluid handled.

A third object is to provide a dispensing cylinder, a large capacity dispensing device, and a method of using a large capacity dispensing device, in which cross contamination of inspection articles can be reliably prevented, the safety of the operator is considered, and ease of handling is achieved.

A fourth object is to provide a dispensing cylinder, a large capacity dispensing device, and a method of using a large capacity dispensing device, which have a simple construction at low price.

A fifth object is to provide a dispensing cylinder, a large capacity dispensing device, and a method of using a large capacity dispensing device, in which a variety of processing of relatively large volumes of fluid can be performed quickly and efficiently for a large number of inspection articles.

DISCLOSURE OF THE INVENTION

In order to solve the technical problems described above, a first aspect of the invention is a dispensing cylinder comprising: a small diameter section, a large diameter section which communicates with the small diameter section and is capable of holding fluids, a sliding section provided in a slidable manner within the large diameter section which enables fluid to be sucked and discharged to and from the large diameter section through the small diameter section, and a connection section which connects the sliding section in a detachable manner to a suction and discharge mechanism which drives the sliding section.

Here, preferably the sliding section slides inside the large diameter section along the axial direction of the large diameter section. Furthermore, preferably the connection section is provided on part of the sliding section that is outside the large diameter section. The tip of the small diameter section is of a size and shape that enables insertion into external containers, and the small diameter section is formed to become sufficiently narrower than the large diameter section so that the sucking and discharging activity of fluids is unimpeded. Furthermore, when performing processing using magnetic particles, preferably the diameter of the small diameter section is such that a magnetic field can be exerted from outside the small diameter section, causing the magnetic particles to attach onto the inside wall of the small diameter section, so as to not cause clogging during suction and discharge of fluids.

The suction and discharge mechanism refers to a mechanism which is provided outside the dispensing cylinder and is responsible for sucking and discharging fluid to and from the large diameter section through the small diameter section. When the connection section is connected to an actuating part of the suction and discharge mechanism, preferably a securing section which secures the large diameter section to a non-actuating part of the suction and discharge mechanism, and prevents the large diameter section from moving when the sliding section is driven, is provided either directly on the large diameter section or on another member provided on the large diameter section. An example of such a securing section includes one or more flanges, protruding from the outside surface of the large diameter section, or from the outside surface of a tube shaped member formed with a narrower diameter than the large diameter section at the opposite end of the large diameter section from the small diameter section and through which the sliding shaft of the sliding section passes. The large diameter section is secured by sandwiching a member provided on a non-actuating part of the suction and discharge mechanism, between the flanges or between a flange and another member.

The end of the large diameter section nearer the small diameter section preferably has a tapered shape, for example a truncated cone shape, to prevent unintended fluid from remaining in the large diameter section, and to allow smooth movement of fluid between the large diameter section and the small diameter section.

According to the first aspect of the invention, fluid is sucked to the large diameter section, where the sliding section is provided, directly through the small diameter section, and held in the large diameter section. Accordingly, a dispensing device which uses this dispensing cylinder does not require in addition to the large diameter section which stores the fluid, a separate cylinder capable of storing an equivalent volume of air, nor the tubing and the like required to connect the two.

Consequently, adjustment of the pressure within the dispensing cylinder when sucking or discharging fluid is sufficient if performed on a volume of air equivalent to the capacity of the small diameter section and the capacity of the large diameter section minimized by sliding of the sliding section. Typically, the volume of a gas varies markedly with variation in temperature and pressure. However, the volume of gas subjected to pressure adjustment in this dispensing cylinder is sufficiently smaller than in a case where a separate cylinder is provided, and it is therefore possible to accurately and precisely control the volume of fluid sucked or discharged, resulting in high quantitativity.

In the dispensing cylinder of the present invention, a sliding section is provided in the large diameter section where suction and discharging of fluid is performed. Accordingly, in a dispensing device using this dispensing cylinder, there is no need to provide in addition to the large diameter section, another cylinder which comprises a mechanism such as a piston and is capable of storing an equivalent capacity, nor the tubing and the like required to connect them, and this suppresses the overall scale of the dispensing device, and allows working space to be used efficiently. Accordingly, the dispensing cylinder is particularly well suited to situations where relatively large volumes of fluid are handled for a large variety of inspection articles.

Furthermore, a connection section which enables the sliding section to be connected in a detachable manner to the suction and discharge mechanism which drives the sliding section is provided on the dispensing cylinder. Accordingly, because the sliding section can be driven automatically by the suction and discharge mechanism instead of manually, and is separate from the suction and discharge mechanism which has a complex driving mechanism, and can be freely detached from this mechanism, the construction can be simplified and manufacturing costs can be reduced. Accordingly, the dispensing cylinder can be used disposably, enabling highly reliable processing to be performed.

Because only the inside of the dispensing cylinder comes into contact with the fluid to be sucked or discharged, that is the liquid or gas, it is possible to almost completely prevent cross contamination, and perform highly reliable processing by replacing the dispensing cylinder in use.

A second aspect of the invention is a dispensing cylinder in which the sliding section comprises; a piston which slides inside the large diameter section, and a rod, one end of which is secured to the piston, and the connection section is provided at the other end of the rod.

Here, preferably a tube supported by the end of the large diameter section with a diameter such that the rod can pass through the inside in an operable manner, is provided coaxially at the end of the large diameter section, extending outward therefrom, thereby preventing the piston from coming away from the large diameter section, and keeping the rod in an operable manner along the axis. At the end of the large diameter section or the tube, a gap is provided which connects the space on the rod side of the large diameter section partitioned off by the piston to the open air. Preferably, as the securing section, a flange is provided on the tube, and for example the flange is held by engaging into the side face of the tube sandwiched between the flange and the end of the large diameter section, to secure the large diameter section to the non-driven part of the suction and discharge mechanism, so as to prevent the large diameter section from moving during sliding of the piston. Using a mechanism which sandwiches the tube rather than the large diameter section itself, by forming the diameter of the rod sufficiently narrower than that of the large diameter section, and accordingly forming the tube narrower than the large diameter section, requires less space and achieves a more secure grip, and has a simpler construction.

According to the second aspect of the invention, the sliding section within the dispensing cylinder has a simple construction, and can therefore be manufactured more economically. This allows the dispensing cylinder to be used in a disposable manner. Accordingly, prevention of cross contamination can be ensured, and highly reliable processing can be performed. Furthermore, by providing the part which keeps the rod in an operable manner, on the large diameter section, the rod is able to operate reliably. Moreover, by using this part to secure the large diameter section, the dispensing cylinder can be reliably fitted by a simple construction to the suction and discharge mechanism.

A third aspect of the invention is a dispensing cylinder in which an engagement section is provided on the outside of the small diameter section of the dispensing cylinder so as to surround the top of the small diameter section, and an opening of a sheath which covers the small diameter section, is fitted to the engagement section.

Preferably the engagement section is provided at a position on the small diameter section that is near to the large diameter section, so that the sheath covers all or most of the small diameter section.

According to the third aspect of the invention, by providing the engagement section for engaging the dispensing cylinder and the sheath, the sheath can be fitted in a manner that covers the small diameter section. As a result, contact with the specimens or reagents by the operator during removal of the used dispensing cylinders can be avoided, which improves safety. Moreover, because the sheath is fitted by engagement with the engagement section, the process can be performed automatically by lowering the small diameter section without human intervention, improving ease of use.

A fourth aspect of the invention is a large capacity dispensing device comprising: one or more dispensing cylinders having a small diameter section, a large diameter section which communicates with the small diameter section and is capable of holding fluids, a sliding section provided in a slidable manner within the large diameter section which enables fluid to be sucked and discharged to and from the large diameter section through the small diameter section, and a connection section which connects the sliding section in a detachable manner to a suction and discharge mechanism which drives the sliding section; a suction and discharge mechanism which connects to the connection section and drives the sliding section; a fitting section which fits the large diameter section in a detachable manner to the suction and discharge mechanism to secure the large diameter section; a container placement area in which a plurality of containers can be placed; and a movement section which enables the one or more dispensing cylinders to move relative to the container placement area.

Here, preferably the range of the movement of the "movement section" covers the entire area of the container placement area. This movement refers not only to movement between containers, that is, horizontal movement, but also to vertical movement of the dispensing cylinders which is required for the insertion and removal of the small diameter section into and from the containers. Preferably the vertical movement section which moves the dispensing cylinders vertically is provided so as to be moved together with the dispensing cylinders, by a horizontal movement section of the dispensing cylinders.

The "fitting section" preferably uses the securing section of the dispensing cylinder so as to secure the dispensing cylinder in a detachable manner to a non-actuating part of the suction and discharge mechanism.

The container placement area preferably contains not only containers with approximately the same capacity as the large diameter section, but also smaller capacity containers. As a result, processing can be performed which requires the extraction of a small volume of a substance from a large volume, for example for the concentration of fluids, or the opposite, dilution. Furthermore, the plurality of containers are preferably arranged in a matrix having a number of rows across equivalent to the number of dispensing cylinders and a number of rows deep equivalent to the number of containers for reagents, specimens, wash liquids, magnetic particle suspensions, product material, and sheaths, and containers for reactions required for the processing or tests performed.

According to the fourth aspect of the invention, the dispensing cylinder, which provides the function of sucking and discharging fluid, can be used in a detachable manner in the large capacity dispensing device. Accordingly, in order to suck or discharge fluid, there is no need for other components in addition to the dispensing cylinder, such as a cylinder equipped with a piston which has equivalent capacity to that of the dispensing cylinder, and the tubing for connecting the other cylinder.

Accordingly, adjustment of the pressure within the dispensing cylinder when sucking or discharging fluid need only be performed on a volume of gas, namely air, in the dispensing cylinder equivalent to the capacity of the small diameter section and the capacity of the large diameter section minimized by sliding of the sliding section. Typically, the volume of a gas varies easily with variation in temperature and pressure. Therefore, by employing a construction in which the volume of gas subjected to pressure adjustment is sufficiently small compared to the volume of fluid handled, the volume of fluid sucked and discharged can be set with greater accuracy and precision.

Furthermore, in the dispensing device of the present invention, a dispensing cylinder is used in which a sliding section which sucks and discharges fluid, is provided in the large diameter section. Accordingly, in the dispensing device of the present invention, because as described above there is no need for other components in addition to the large diameter section, such as another cylinder which has approximately the same capacity as the large diameter section and has a mechanism such as a piston, nor the tubing required to connect these cylinders, the overall scale of the dispensing device can be suppressed, and working space can be used efficiently. Accordingly, the dispensing device of the present invention is of particular advantage when handling comparatively large volumes of fluids for a wide variety of inspection articles.

Furthermore, in the dispensing device of the present invention, because all components that come into contact with fluids including liquid or gas are exchangeable, cross contamination can be almost completely prevented, and highly reliable processing can be performed.

Furthermore, because the installation and removal of the cylinders is performed manually, there is no need to place unused and used dispensing cylinders in the container work area. Accordingly, the work area required is reduced, and even when handling a large variety of relatively large volumes of fluid, the scale of the device is suppressed, and the work area can be used efficiently. Furthermore, a wide variety of processing of relatively large volumes of fluid for a large number of inspection articles can be performed quickly and efficiently.

By placing the containers containing the various reagents and specimens in the container placement area in advance, the device can complete a processing task from beginning to end in a consistent manner, resulting in high operating efficiency.

A fifth aspect of the invention is a large capacity dispensing device comprising a gap elimination mechanism which eliminates a gap between the connection section of the dispensing cylinder, and a connection target section provided on the suction and discharge mechanism which connects to the connection section.

Because the construction of the connection section of the dispensing cylinder is such that the connection section is connected to the connection target section of the suction and discharge mechanism by a manual operation performed by the operator, a gap is provided between the connection section and the connection target section to facilitate this task. If an attempt is made to transmit the action of the suction and discharge mechanism to the sliding section of the dispensing cylinder while this gap is present, there is a danger of juddering occurring between the connection section and the connection target section, preventing fluid from being sucked and discharged in exact volumes. Accordingly, the gap elimination mechanism for eliminating the gap is provided.

According to the fifth aspect of the invention, by providing a gap between the connection section of the dispensing cylinder and the connection target section of the suction and discharge mechanism, connection between the connection section and the connection target section can be made easily. By further providing a gap elimination mechanism which automatically eliminates this gap, the gap between the connection section and the connection target section can be eliminated, and the transmission of force from the suction and discharge mechanism to the sliding section can be performed reliably. Consequently, precise and accurate control of the amount of fluid sucked or discharged from the dispensing cylinder can be performed, enabling highly reliable processing.

A sixth aspect of the invention is a large capacity dispensing device in which the small diameter section of the dispensing cylinder comprises an engagement section formed so as to protrude outward from the small diameter section, and the container placement area contains in addition to a plurality of containers, one or more sheaths which can be fitted by engaging an opening thereof with the engagement section so that the sheath covers the small diameter section of the dispensing cylinder, arranged in a manner that enables fitting to the small diameter section.

According to the sixth aspect of the invention, the container placement area contains, in addition to the containers, sheaths which can be fitted to the small diameter section of the dispensing cylinder so as to cover the small diameter section. The sheaths have a sufficiently small capacity compared to the dispensing cylinder. Accordingly, by installing and removing the dispensing cylinders manually and automating only the fitting of the sheaths, instead of placing the dispensing cylinders themselves in the container placement area and automating their installation and removal, and preventing direct contact between the hand of the operator and the small diameter section, the area used for the installation and removal of dispensing cylinders can be minimized, and hence the work area can be utilized more efficiently.

A seventh aspect of the invention is a large capacity dispensing device in which a magnetic section capable of exerting and removing a magnetic field into the small diameter section of the dispensing cylinder, is provided at a predetermined position in the vicinity of a path of vertical movement of the small diameter section.

Preferably, the magnetic section, and therefore the magnetic activity region on the path of vertical movement where the magnetic section is capable of exerting a magnetic field, is provided in a manner that enables movement between containers, that is movement together with the dispensing cylinders when the dispensing cylinders move horizontally. Consequently, magnetic particles can be isolated from containers with various contents by using magnetic force to cause the magnetic particles to attach to the side wall of the small diameter section. Preferably, part of the small diameter section, for example the top section assuming the small diameter section is divided into a top section near the large diameter section and a bottom section at the opposite end to the large diameter section, is formed slightly more thickly than the other region, for example the bottom section of the small diameter section, and the magnetic field produced by the magnetic section is exerted on this region, for example the top section. As a result, when a magnetic field is exerted on the magnetic particles suspended in the solution causing the magnetic particles to attach to the inside wall in that region, for example the top section, a situation in which the small diameter section becomes clogged by the magnetic particles can be prevented. The "predetermined position" mentioned above is preferably a position from which the small diameter section can suck and discharge fluid to and from the containers provided in the container placement area. As a result, a magnetic field can be exerted during the suction and discharge of fluids.

According to the seventh aspect of the invention, a magnetic field can be exerted into the small diameter section in the path of vertical movement of the small diameter section. Accordingly, a magnetic field can be reliably exerted into the small diameter section no matter how large the capacity of the large diameter section. Furthermore, by using as the predetermined position and the magnetic activity region, positions from where the dispensing cylinder can suck and discharge fluid, a magnetic field can be exerted when the suction and discharge of fluids is performed, and consequently a magnetic field can be exerted into all of the magnetic particles contained in the fluid, which results in high efficiency. Furthermore, because a magnetic field can be exerted simultaneously with suction or discharge, the processing can be completed quickly.

Furthermore, by using magnetic particles, various processing including isolation, concentration and dilution of a target substance can be performed quickly and easily.

An eighth aspect of the invention is a large capacity dispensing device comprising an optical measuring section capable of optically measuring a fluid level in the dispensing cylinder.

In this case, preferably the wall of the dispensing cylinder is formed from a transparent or semitransparent material. Furthermore, preferably the optical measuring section can move in the horizontal direction together with the dispensing cylinders. Furthermore, preferably the optical measuring section is capable of moving up and down independently from the dispensing cylinders. In addition, to provide clarity for the measurement of the fluid volume in the dispensing cylinder, preferably an irradiation section is provided which irradiates light onto the dispensing cylinders.

According to the eighth aspect of the invention, by optically measuring the fluid volume of the dispensing cylinders when suction or discharging is performed by the dispensing cylinders, checks relating to the suction and discharge operations such as the volume of fluid in the dispensing cylinder after suction, or the fluid remaining after discharging can be performed, and consequently, even greater quantitativity is obtained, and highly reliable processing can be performed.

A ninth aspect of the invention is a large capacity dispensing device in which the optical measuring section comprises a CCD camera with an optical axis along an axial direction of the dispensing cylinder, and a mirror which reflects light from the dispensing cylinder into the CCD camera.

According to the ninth aspect of the invention, by providing a mirror, the light from the dispensing cylinder can be altered to the optical axis direction of the CCD camera. Accordingly, by setting the optical axis of the CCD camera to run parallel to the axial direction of the dispensing cylinder, the scale of the device can be suppressed, and working area can be utilized efficiently.

Instead of providing a CCD camera and mirror as the optical measuring section, the presence or absence of fluid inside the large diameter section and the small diameter section may be detected by providing two pairs of light emitting elements and light receiving elements for each dispensing cylinder so as to be on either side of the dispensing cylinder. In this case, because the construction is simpler than if a CCD camera and mirror were provided, and there is no need for a mechanism to move the camera and the like along the dispensing cylinder, the space of the device and the manufacturing costs can be reduced.

A tenth aspect of the invention is a large capacity dispensing device in which the optical measuring device is capable of relative movement relative to two or more dispensing cylinders.

Because it is impossible to measure two or more dispensing cylinders simultaneously if one of the cylinders has a larger capacity, the optical measuring device is moved in order to measure one or a small number of dispensing cylinders at a time.

According to the tenth aspect of the invention, by providing a CCD camera capable of moving relative to two or more dispensing cylinders, even when there are a plurality of large capacity dispensing cylinders, images of the required parts of each dispensing cylinder can be taken using one CCD camera.

An eleventh aspect of the invention is a large capacity dispensing device in which an identifier is affixed to a container placed in the container placement area which identifies the container, and which comprises a readout section which reads the identifier affixed to the container.

Here, one example of an identifier is a barcode. The readout section is capable of moving together with the dispensing cylinders or independently of the dispensing cylinders. When reading identifier affixed to the side of a container, preferably the readout section is capable of moving vertically independently of the dispensing cylinders. Movement of the readout section may also be performed together with or independent of the optical measuring section.

According to the eleventh aspect of the invention, by affixing identifiers to the containers and reading those identifiers, the contents of the containers can be recognized automatically without increasing the burden on the user, and highly reliable processing can be performed.

A twelfth aspect of the invention is a large capacity dispensing device in which the identifier is affixed to a tag provided in a detachable manner on the container.

According to the twelfth aspect, because the identifier is affixed to a removable tag provided on the container and not to the container itself, the identifier can be attached or removed easily, and containers or identifiers can be reused, which improves ease of use.

A thirteenth aspect of the invention is a large capacity dispensing device in which the container placement area comprises a temperature adjustment section which adjusts the temperature of containers placed in the area.

According to the thirteenth aspect, by providing a temperature adjustment section which adjusts the temperature of the containers placed in the area, the large capacity dispensing device can be used to perform required processing in succession in a consistent manner, and can perform a wide variety of processing.

A fourteenth aspect of the invention is a method of using a large capacity dispensing device comprising: a suction and discharge step for sucking or discharging a predetermined fluid to or from a container by using a container placed in a container placement area, and one or more dispensing cylinders having a small diameter section, a large diameter section which communicates with the small diameter section and is capable of holding fluid, a sliding section provided in a slidable manner within the large diameter section which enables fluid to be sucked and discharged to and from the large diameter section through the small diameter section, and a connection section which connects the sliding section in a detachable manner to a suction and discharge mechanism which drives the sliding section; and a movement step for moving the dispensing cylinder relative to the container placement area.

To perform suction and discharge processes using a dispensing cylinder, preparation is required in terms of installing the dispensing cylinders in the large capacity dispensing device, connecting the connection sections of the installed cylinders to the suction and discharge mechanism, and placement of the containers.

According to the fourteenth aspect of the invention, in the same manner as the fourth aspect of the invention, the dispensing cylinder, which provides the function of sucking and discharging fluid, can be used in a detachable manner in the large capacity dispensing device. Accordingly, in order to suck or discharge fluid, there is no need for other components in addition to the dispensing cylinder, such as a cylinder equipped with a piston which has equivalent capacity to that of the dispensing cylinder, and the tubing for connecting the other cylinder.

Accordingly, adjustment of the pressure within the dispensing cylinder when sucking or discharging fluid need only be performed on a volume of gas, namely air, in the dispensing cylinder equivalent to the capacity of the small diameter section and the capacity of the large diameter section minimized by sliding of the sliding section. Typically, the volume of a gas varies easily with variation in temperature and pressure. Therefore, by employing a construction in which the volume of gas subjected to pressure adjustment is sufficiently small compared to the volume of fluid handled, the volume of fluid sucked and discharged can be set with greater accuracy and precision.

Furthermore, in the dispensing device of the present invention, a dispensing cylinder is used in which a sliding section which sucks and discharges fluid is provided in the large diameter section. Accordingly, in the dispensing device of the present invention, because as described above there is no need for other components in addition to the large diameter section, such as another cylinder which has approximately the same capacity as the large diameter section and has a mechanism such as a piston, nor the tubing required to connect these cylinders, the overall scale of the dispensing device can be suppressed, and working space can be used efficiently. Accordingly, the dispensing device of the present invention is of particular advantage when handling comparatively large volumes of fluids for a wide variety of inspection articles.

Furthermore, in the dispensing device of the present invention, because all components that come into contact with fluids including liquid or gas are exchangeable, cross contamination can be almost completely prevented, and highly reliable processing can be performed.

Furthermore, because the installation and removal of the cylinders is performed manually, there is no need to place unused and used dispensing cylinders in the container work area. Accordingly, the work area required is reduced, and even when handling a large variety of relatively large volumes of fluid, the scale of the device is suppressed, and the work area can be used efficiently. Furthermore, a wide variety of processing of relatively large volumes of fluid for a large number of inspection articles can be performed quickly and efficiently.

Furthermore, by placing the containers containing the various reagents and specimens in the container placement area in advance, the device can complete a processing task from beginning to end in a consistent manner, resulting in high operating efficiency.

A fifteenth aspect of the invention is a method of using a large capacity dispensing device comprising a sheath fitting step for moving the dispensing cylinder to a position in the container placement area where the sheath is placed, and fitting the sheath by lowering the dispensing cylinder so that the sheath covers the small diameter section of the dispensing cylinder.

This sheath fitting step is required when the operator removes the used dispensing cylinders once a series of processes have been completed and the product material has been placed in a predetermined container.

According to the fifteenth aspect of the invention, in the same manner as the sixth aspect, the container placement area contains, in addition to the containers, sheaths which can be fitted to the small diameter section of the dispensing cylinder so as to cover the small diameter section. The sheaths have a sufficiently small capacity compared to the dispensing cylinder. Accordingly, by installing and removing the dispensing cylinders manually and automating only the fitting of the sheaths, instead of placing the dispensing cylinders themselves in the container placement area and automating their installation and removal, and preventing direct contact between the hand of the operator and the small diameter section, the area used for the installation and removal of dispensing cylinders can be minimized, and the work area can be utilized more efficiently.

A sixteenth aspect of the invention is a method of using a large capacity dispensing device comprising an operation checking step for, during the suction and discharge step, checking the result of suction or discharge, by optically measuring a fluid volume within the dispensing cylinder.

According to the sixteenth aspect, as with the eighth aspect, by optically measuring the fluid volume of the dispensing cylinders when suction or discharging is performed by the dispensing cylinders, checks relating to the suction and discharge operations such as the volume of fluid in the dispensing cylinder after suction, or the fluid remaining after discharging can be performed, and consequently, even greater quantitativity is obtained, and highly reliable processing can be performed.

A seventeenth aspect of the invention is a method of using a large capacity dispensing device comprising a container placement checking step for checking the placement of a container in the container placement area, by reading an identifier of a container placed in the area.

According to the seventeenth aspect, as with the eleventh aspect, by affixing identifiers to the containers and reading those identifiers, the contents of the containers can be recognized automatically without increasing the burden on the user, and highly reliable processing can be performed.

An eighteenth aspect of the invention is method of using a large capacity dispensing device comprising a step for adjusting the temperature of a fluid by using the dispensing cylinder to transfer a fluid to a container where a temperature adjustment section which adjusts the temperature of the container is provided.

According to the eighteenth aspect, in the same manner as the thirteenth aspect, by providing a temperature adjustment section which adjusts the temperature of the containers placed in the area, the large capacity dispensing device can be used to perform required processing in succession in a consistent manner, and can perform a wide variety of processing.

A nineteenth aspect of the invention is a method of using a large capacity dispensing device comprising a gap removal step for eliminating a gap between a connection section of the dispensing cylinder and a connection target section provided on the suction and discharge mechanism which connects to the connection section.

According to the nineteenth aspect, in the same manner as the fifth aspect, by providing a gap between the connection section of the dispensing cylinder and the connection target section of the suction and discharge mechanism, connection between the connection section and the connection target section can be made easily. By further providing a gap elimination mechanism which automatically eliminates this gap, the gap between the connection section and the connection target section can be eliminated, and the transmission of force from the suction and discharge mechanism to the sliding section can be performed reliably. Consequently, precise and accurate control of the amount of fluid sucked or discharged from the dispensing cylinder can be performed, enabling highly reliable processing.

A twentieth aspect of the invention is a method of using a large capacity dispensing device comprising; a step for moving a small diameter section of a dispensing cylinder vertically to a magnetic activity region provided in a path of vertical movement of the small diameter section, and a step for exerting a magnetic field into or removing a magnetic field from the small diameter section in the magnetic activity region when a solution in which magnetic particles are suspended is sucked or discharged using a dispensing cylinder.

Here, the height at which the magnetic activity region and therefore the magnetic source of the magnetic section is provided is preferably within such a range from the container placement area that a magnetic field can be exerted into the small diameter section when the tip of the small diameter section is inserted into a container and suction or discharge of fluid is performed. Furthermore, the "magnetic particles" bond or are capable of bonding with a predetermined substance such as the target substance.

According to the twentieth aspect of the invention, in the same manner as the seventh aspect of the invention, a magnetic field can be exerted into the small diameter section in the path of vertical movement of the small diameter section. Accordingly, a magnetic field can be reliably exerted into the small diameter section no matter how large the capacity of the large diameter section. Furthermore, by using as the predetermined position and the magnetic activity region, positions from where the dispensing cylinder can suck and discharge fluid, a magnetic field can be exerted when the suction and discharge of fluids is performed, and consequently a magnetic field can be exerted into all of the magnetic particles contained in the fluid, which results in high efficiency. Furthermore, because a magnetic field can be exerted simultaneously with suction or discharge, the processing can be completed quickly.

Furthermore, by using magnetic particles, various processing including isolation, concentration and dilution of a target substance can be performed quickly and easily.

BEST MODE FOR CARRYING OUT THE INVENTION

As follows is a description of a cylinder, a large capacity dispensing device, and a method of using a large capacity dispensing device according to embodiments of the present invention, with reference to the drawings. It should be understood that the descriptions of the embodiments are exemplary of the invention and are not to be considered as limiting, unless particularly specified.

Figure 1:
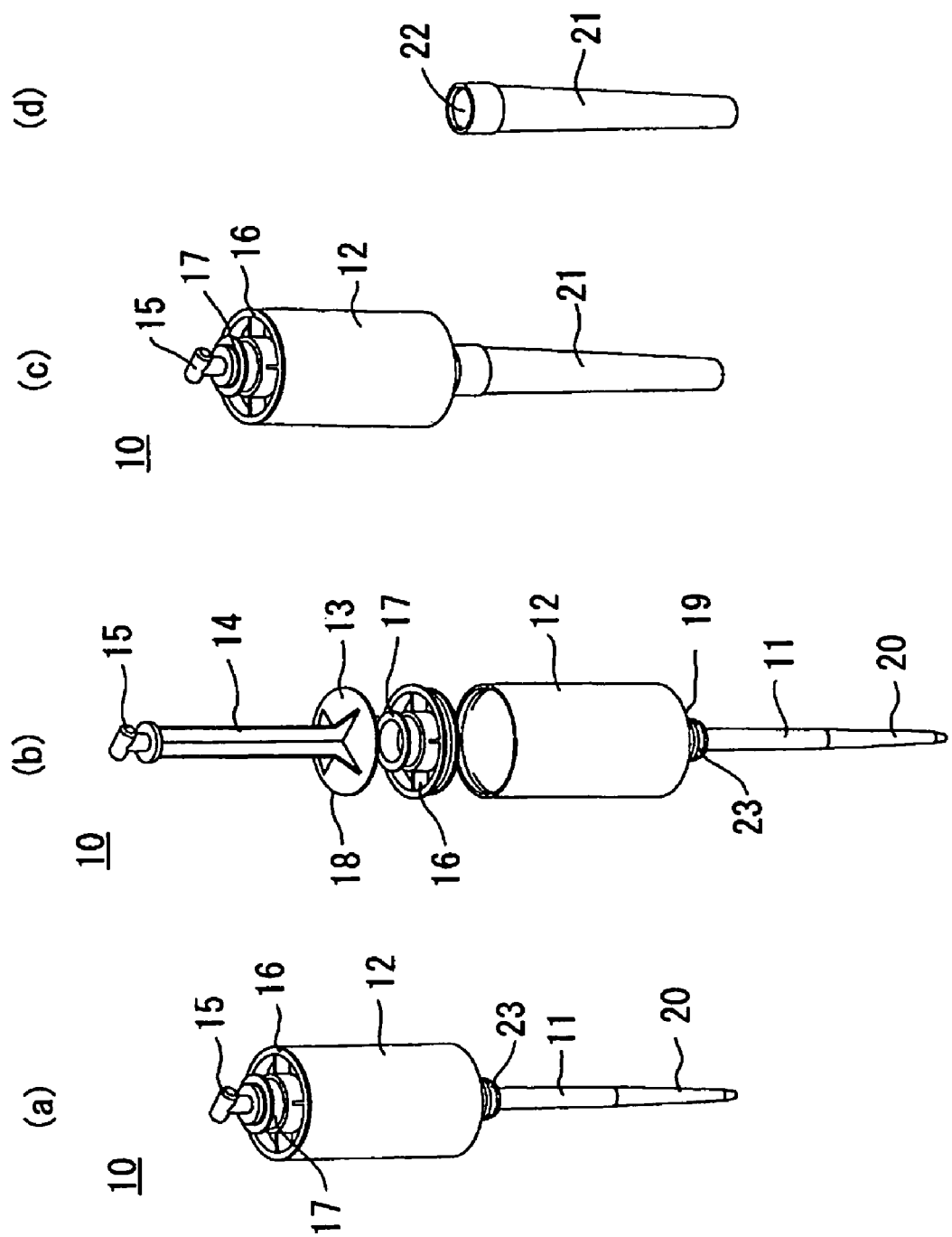
FIG. 1 is a diagram showing a dispensing cylinder according to an embodiment of the present invention.

FIG. 1 shows a dispensing cylinder 10 according to an embodiment. FIG. 1 (a) shows a perspective view of the outward appearance of the dispensing cylinder 10, and FIG. 1 (b) is an exploded perspective view.

The dispensing cylinder 10 comprises: a tapered approximately cylindrical small diameter section 11; an approximately cylindrical large diameter section 12 which communicates with the small diameter section 11 and is capable of holding fluid; a disk shaped piston 13 slidably provided within the large diameter section 12 corresponding to a sliding section the sliding section which enables fluid to be sucked to and discharged from the large diameter section 12 through the small diameter section 11, whose periphery is in intimate contact with the inside wall of the large diameter section 12; a rod 14 provided with one end secured to the piston 13; and a T shaped end section 15 which is formed in an approximate T shape when viewed front on and is formed at the other end of the rod 14 which is outside the large diameter section 12, serving as a connection section which connects the piston 13 in a detachable manner to an actuating part of a suction and discharge mechanism (described below) which drives the piston 13.

A head 16 which covers the opening in the large diameter section 12 is provided at the top end of the large diameter section 12, and a flange tube 17 is provided at the center of the head 16 protruding outward concentrically with the large diameter section 12. The rod 14 passes through both the head 16 and the flange tube 17, and a flange is provided at the top end of the flange tube 17. The T shaped end section 15 on the other end of the rod 14 is located outside the flange tube 17. The flange tube 17 retains the rod 14 in an operable manner, and also corresponds to the securing section which is used to attach the large diameter section 12 to the nonactuating part of the suction and discharge mechanism.

The rod 14 is cross-shaped in cross section, so that a gap is provided between the rod 14 and the flange tube 17, and the space on the rod 14 side of the large diameter section 12 partitioned off by the piston 13 is communicated with the open air through the gap between the rod 14 and the flange tube 17. Preferably one or more rows of grooves are formed in the periphery 18 of the piston 13 to improve watertightness. A bottom end section 19 of the large diameter section 12 is approximately cone shaped, and a small capacity void remains in this bottom end section 19 even when the piston 13 is at bottom dead center. Accordingly, when using the dispensing cylinder 10 according to the present embodiment, pressure adjustment is performed for a volume of air equivalent to the total of the capacity of the bottom end section 19 and the capacity of the small diameter section 11. Note that a gap may be provided in the head 16 instead of between the rod 14 and the flange tube 17.

The small diameter section 11 has a tip section 20 capable of insertion into various containers, and is provided with an outer ring section 23 serving as an engagement section which engages with an opening 22 of a sheath 21, with a slightly larger diameter than the small diameter section 11, and in which one or more thin axial notches are formed. The outer ring section 23 protrudes downward from the bottom end section 19 so as to enclose the top of the small diameter section 11. To prevent the sheath 21 from falling off, a raised bar which engages with an annular groove on the inner circumference of the opening of the sheath 21, is provided on the outer circumference of the outer ring section 23, and the diameter of the outer ring section 23 is of a size that engages with the opening of the sheath 21. Here, the small diameter section 11, the large diameter section 12, and the outer ring section 23 are made of transparent or semitransparent members, for example glass or resins such as polyethylene, acrylic, polyester and polystyrene. The capacity of the large diameter section 12 is, for example, 50 milliliters.

FIG. 1 (c) shows the dispensing cylinder 10 in a state where the sheath 21 is fitted with the opening section of the sheath 21 engaged with the outer ring section 23, and FIG. 1 (d) shows the sheath 21.

Figure 2:
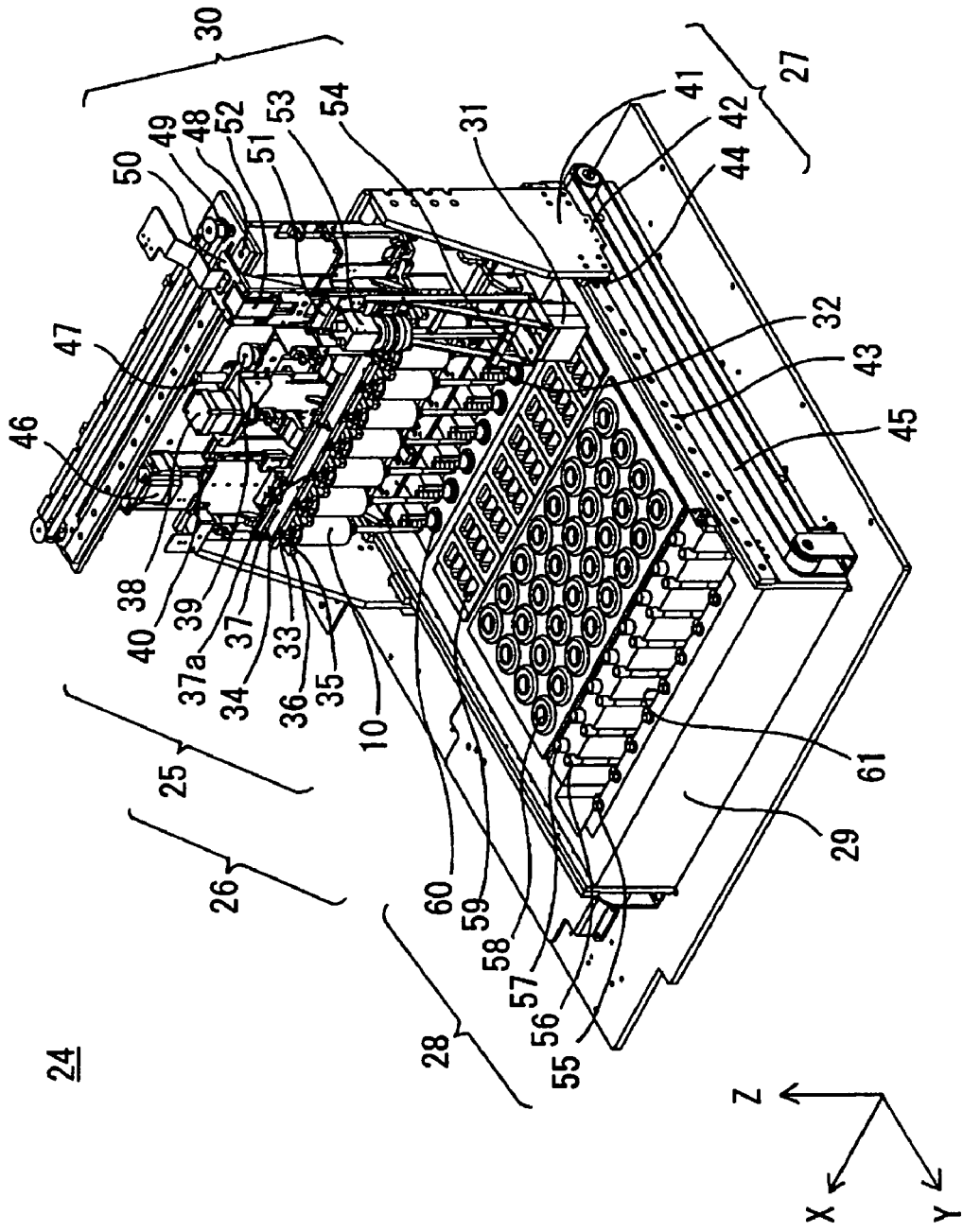
FIG. 2 is a perspective view of a large capacity dispensing device according to an embodiment of the present invention.

FIG. 2 is a partial overall perspective view of a large capacity dispensing device 24 according to a second embodiment.

The large capacity dispensing device 24 comprises a main body section 26, in which is provided; a series of eight dispensing cylinders 10 arranged in a row along a line extending in the X axis direction in the figure, and a suction and discharge mechanism 25, in which the eight dispensing cylinders 10 are fitted in a detachable manner, which connects to each of the connection sections 15 and drives the pistons 13 of the dispensing cylinders 10. The large capacity dispensing device 24 further comprises: the main body section 26, and thus the dispensing cylinders 10, provided in a vertically movable manner (in the Z axis direction in the figure); a Y axis carriage 27 which enables the main body section 26, and thus the dispensing cylinders 10, to move along the Y axis direction in the figure; and a container placement stage 29 comprising a container placement area 28 where a plurality of containers are placed.

Furthermore, the large capacity dispensing device 24 comprises: an optical measurement section 30 which optically measures the fluid level to allow the amount of fluid in the series of eight dispensing cylinders 10 to be known; a barcode reader 31 which reads barcodes affixed to the containers; and a magnetic section 32 which exerts a magnetic field into the small diameter section 11.

The main body section 26 is composed of the suction and discharge mechanism 25 and the series of eight dispensing cylinders 10.

The suction and discharge mechanism 25 comprises a plate 34 which belongs to the actuating part, in which eight T-shaped cavities 33 which are approximately T-shaped when viewed front on are provided as eight connection target sections that engage with the eight T shaped end sections 15 to be connected with the eight T shaped end sections 15 by frictional force; and eight pairs of cylindrical sandwiching members 35 of a thickness that fits between the flange of the flange tube 17 and the head 16 of the large diameter section 12, which hold the dispensing cylinders 10 by elastically energizing the outer periphery of the dispensing cylinder 10 from both sides, serving as the fitting section provided on the non-actuating part.

Furthermore, the suction and discharge mechanism 25 comprises: eight semicircular guide sections 36 cut into the guide plate, which contact the outer peripheral surface of the large diameter sections 12 of the dispensing cylinders 10 and guide the dispensing cylinders 10; an upper plate 37 belonging to the actuating part above the plate 34 which is secured to the plate 34 so as to cover the T-shaped cavities 33 from above, and has eight thin hole shaped gaps along the Y axis direction provided at positions corresponding to the T-shaped cavities 33 such that the T shaped end sections 15 easily engage with the T-shaped cavities 33; and a gap elimination plate 37a belonging to the actuating part which is provided as a gap elimination mechanism which removes the gaps to prevent vertical juddering of the T shaped end section 15 that occurs due to the gap, so as to ensure the reliable transmission of power from the suction and discharge mechanism to the piston 13, and is capable of movement in the Y axis direction within the gap. The gap elimination plate 37a is driven by a motor not shown in the diagram, and moves vertically together with the plate 34 and the like.

The suction and discharge mechanism 25 comprises: a motor 38 which drives the piston 13 by moving the plate 34 and the upper plate 37 and the like of the actuating part vertically; a ball screw 39 which is driven rotationally by the motor 38; and a main body frame 40, belonging to the non-actuating part which holds the eight dispensing cylinders 10, in which the motor 38, the ball screw 39, the sandwiching member 35, and the guide section 36 are provided.

The Y axis carriage 27 comprises: a frame 41 which supports the main body section 26 in a vertically movable manner; a timing belt 45 provided below the frame 41 on the container placement stage 29 so as to enable movement of the Y axis carriage 27; a leg section 42 attached to the timing belt 45; a guide section 44 which contacts a rail 43 provided on the container placement stage 29 along the Y axis direction and guides the travel of the frame 41; a Z axis elevation motor 46 secured to the frame 41 which drives the main body section 26 vertically; and a Z axis elevation mechanism ball screw 47 belonging to the vertical movement section which is provided on the frame 41, is driven rotationally by the Z axis elevation motor 46, and drives the main body section 26 vertically.

The optical measurement section 30 comprises: an X axis carriage 50 guided by a rail 48 secured to the frame 41 of the Y axis carriage 27 along the X axis direction and capable of traveling above the Y axis carriage 27 along the X axis direction by means of the timing belt 49 provided along a rail 48; a support frame 51 capable of vertical movement relative to the X axis carriage 50; a motor 52 which moves the support frame 51 vertically; and a CCD camera 53 and a mirror 54 attached to the support frame 51. The barcode reader 31 is provided below the support frame 51 and is capable of vertical movement relative to the X axis carriage 50, in the same manner as the CCD camera 53 and the mirror 54. The CCD camera 53, the mirror 54 and the barcode reader 31 are independent of the dispensing cylinders 10 in terms of movement in the X axis direction and the vertical direction.

Eight cylindrical backlight sections (not shown in the diagram) which have approximately the same length in the axial direction as the large diameter sections 12 of the dispensing cylinders 10, are provided on the frame 41 of the Y axis carriage 27 on the surface facing the dispensing cylinders 10, each at a position corresponding to a dispensing cylinder 10. Consequently strong light can enter the CCD camera 53. The backlight sections correspond to the illumination section.

The container placement area 28 contains eight rows of respective various types of containers 55, 56, 57, 58, 59 and 60. Reference numeral 61 in the figure indicates a cavity in the container placement stage 29 of a size that allows the barcode reader 31 affixed to the containers 55 and 56 to be inserted, positioned so as to enable the barcodes affixed to the containers 55 and 56 to be read by the barcode reader 31.

Figure 3:
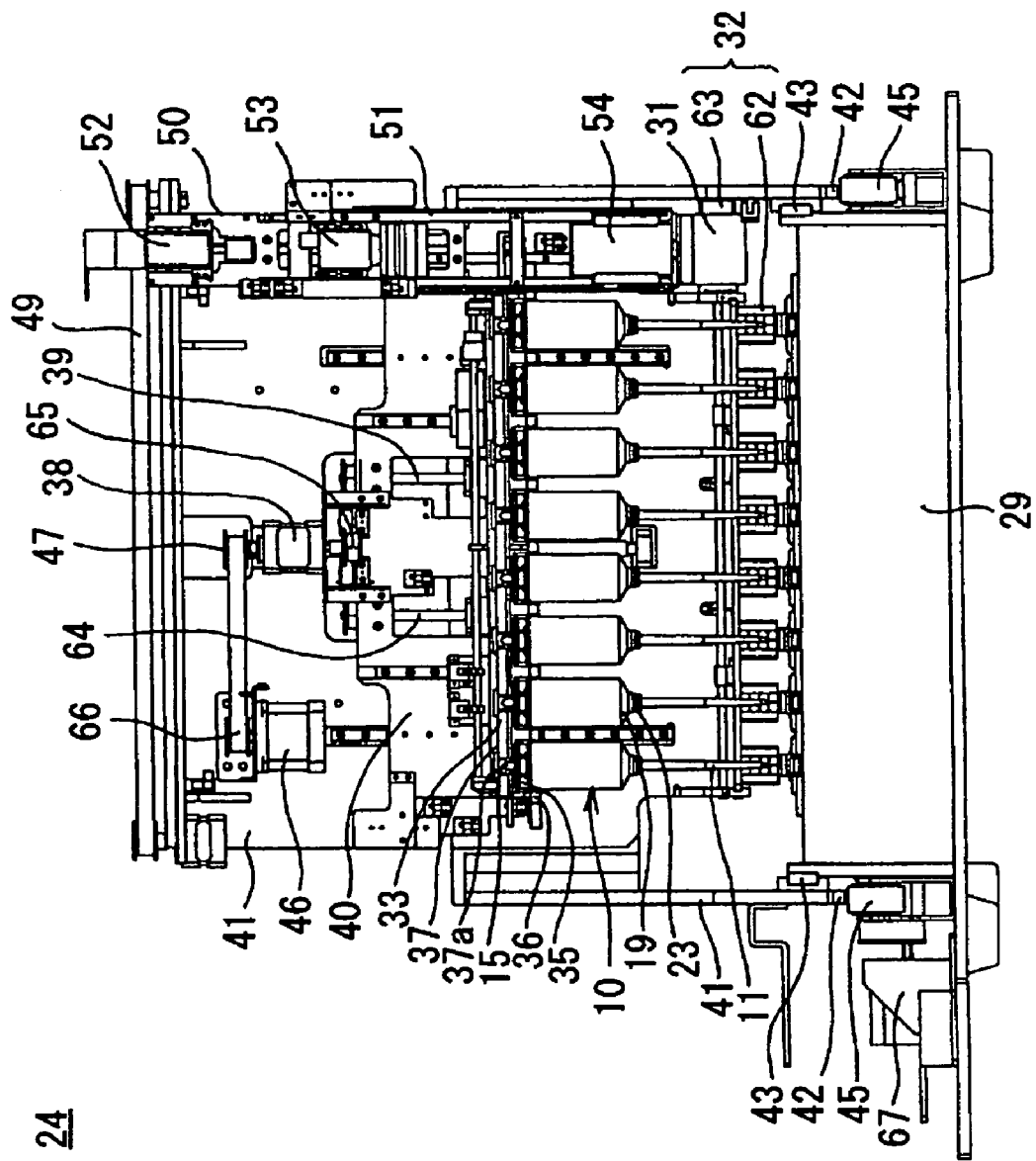
FIG. 3 is a front view of a large capacity dispensing device according to an embodiment of the present invention.

FIG. 3 is a front view of the large capacity dispensing device 24.

The magnetic section 32 is provided on the frame 41 of the Y axis carriage 27. The magnetic section 32 has a magnetic activity region in the possible path of vertical movement corresponding to the eight vertically moving dispensing cylinders 10, at a relatively lower predetermined position. The magnetic activity region is positioned at such a height that when the tip section 20 of the small diameter section 11 is inserted into a container in the container placement area, suction and discharge of fluid to and from the container can be performed. The magnetic section 32 comprises: eight magnetic blocks 62 capable of moving a predetermined distance in the Y direction to be able to move towards or away from the small diameter sections 11 and thereby apply or remove a magnetic field to or from each of the small diameter sections 11 positioned in the magnetic activity region; and a motor 63 which drives the magnetic blocks 62 towards or away from the small diameter sections 11. Because the magnetic section 32 is provided on the Y axis carriage 27, the magnetic section 32 can move together with the dispensing cylinders 10 by movement of the Y axis carriage 27.

Furthermore, rotation of the motor 38 for driving the pistons is transmitted to the ball screws 39 and 64 by a sprocket 65 via a roller and a timing belt. Reference numeral 66 indicates a timing belt which together with a sprocket transmits the rotation of the Z axis elevation motor 46 to the ball screw 47.

Furthermore, reference numeral 67 in the diagram indicates a motor which drives the timing belt 45 rotationally to move the Y axis carriage 27.

Figure 4:
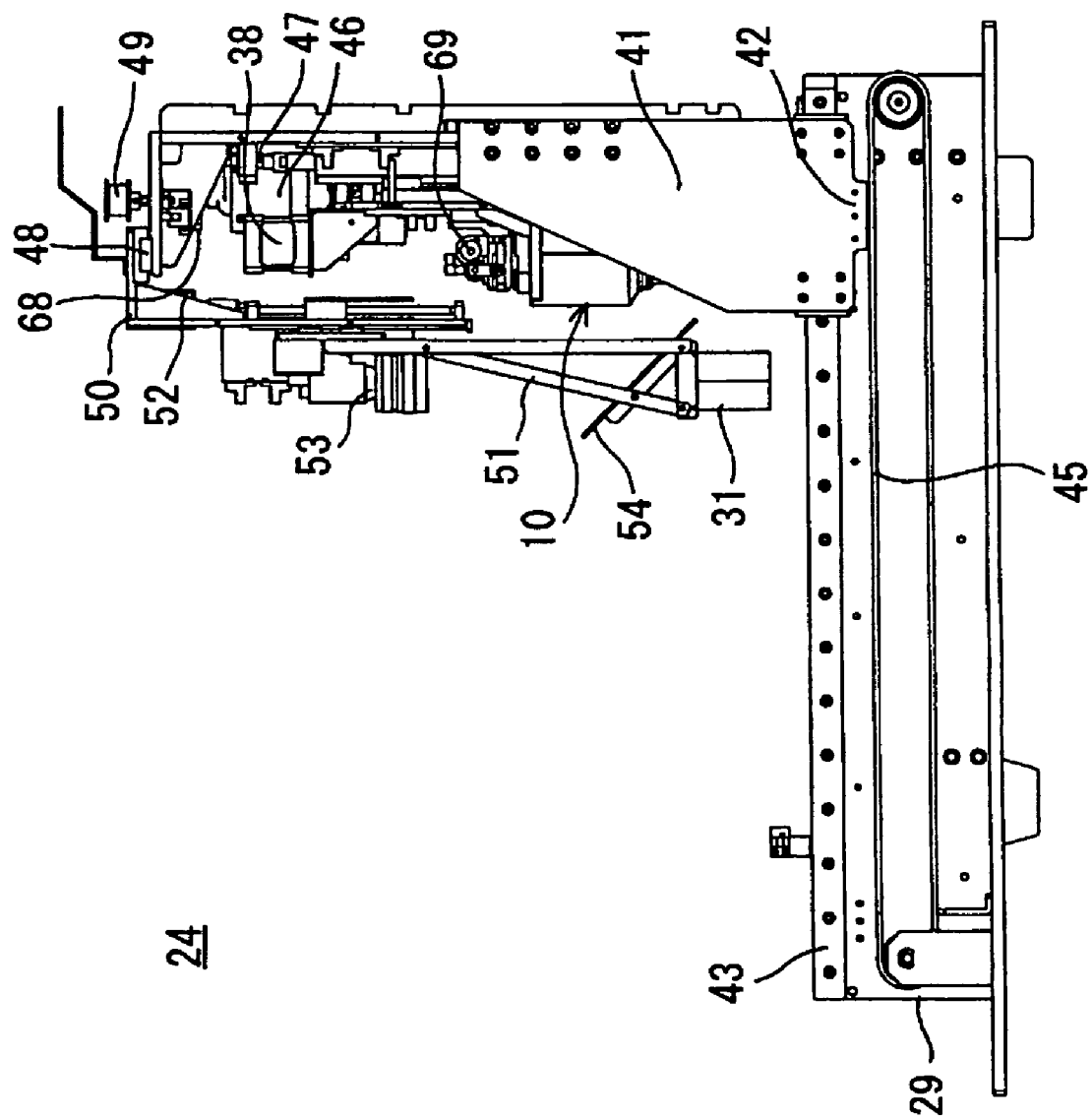
FIG. 4 is a side view of a large capacity dispensing device according to an embodiment of the present invention.

FIG. 4 is a side view of the large capacity dispensing device 24 according to the embodiments.

Reference numeral 68 in the diagram indicates a motor which uses a sprocket to rotationally drive the timing belt 49 which moves the X axis carriage 50.

Reference numeral 69 in the diagram indicates a member which moves each sandwiching member 35 an extremely small distance so that the sandwiching members 35 clamp the flange tubes 17 in an elastically energized state.

Figure 5:
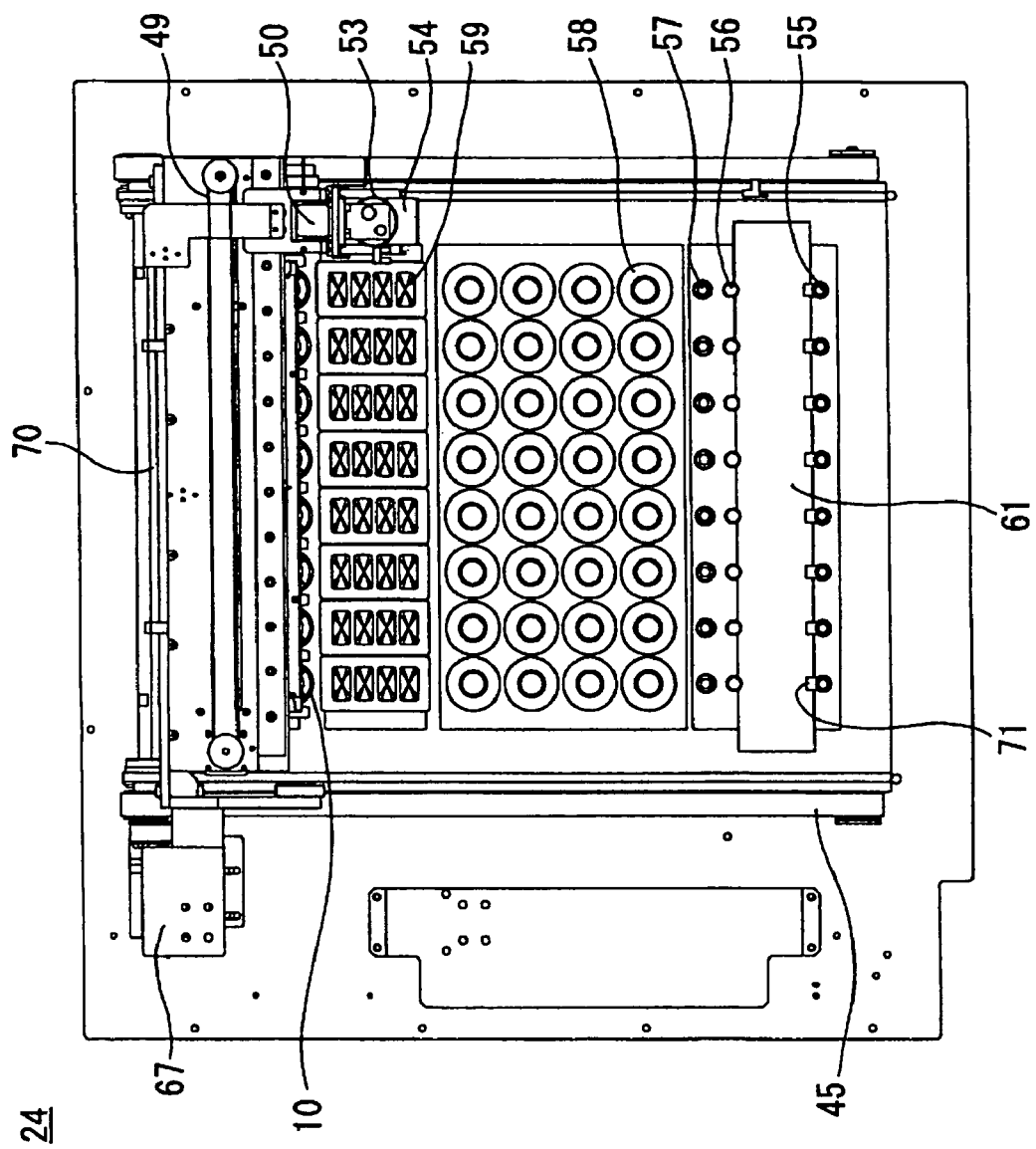
FIG. 5 is a plan view of a large capacity dispensing device according to an embodiment of the present invention.

FIG. 5 shows a plan view of the large capacity dispensing device 24 according to the embodiments. In the diagram, reference numeral 70 indicates a rotating shaft for transmitting the rotational drive of the motor 67 which drives the timing belt 45, to the timing belt 45 provided on the opposite surface of the container placement stage 29.

As described above, containers 55, 56, 57, 58, 59 and 60 are arranged on the container placement stage 29. Of these, the containers 55 hold product material. Tags 71 to which are affixed the above described barcodes serving as the identifiers, are provided in a detachable manner on the containers 55. Barcodes serving as identifiers are also attached to the containers 56 which contain specimens.

The containers 57 contain sheaths 21 which can be fitted to the small diameter section 11 of the dispensing cylinders 10 by inserting the small diameter section 11 into the containers 57. The containers 58 are 50 milliliter containers which hold a relatively large volume of fluid corresponding to the capacity of the large diameter section 12. The containers 59 are 15 milliliter prepacked reagent trays which are prepacked with relatively small volumes of a predetermined reagent. The containers 60 hold predetermined reagents. In the container placement stage 29, a heating block (not shown) which heats the containers 60 is provided either so as to surround the containers 60 or near the containers 60.

Figure 6:
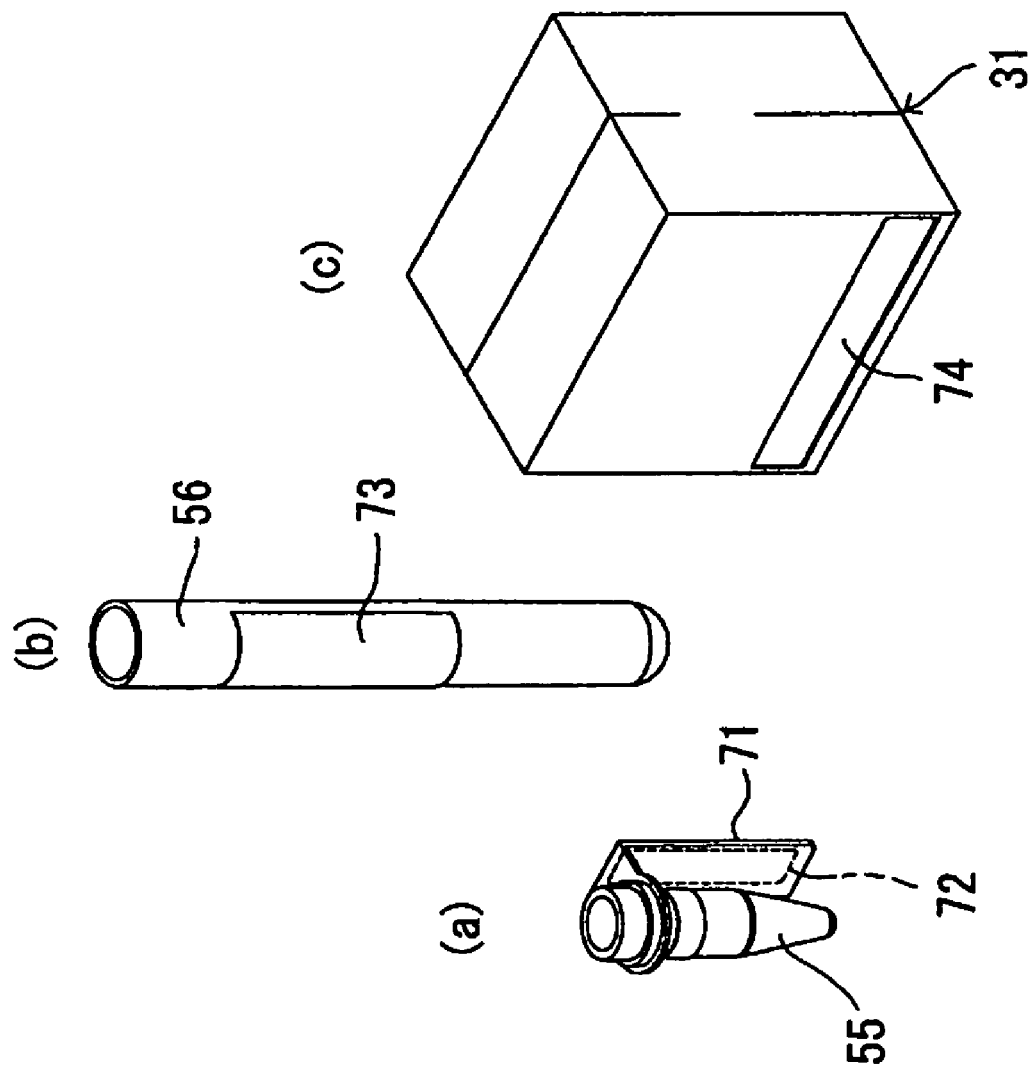
FIG. 6 is a diagram showing a container and barcode reader according to an embodiment of the present invention.

FIGS. 6 (*a*) and (*b*) show the barcode 72 affixed to the tag 71 detachably attached to the container 55, and the barcode 73 affixed to the container 56. FIG. 6 (*c*) shows the barcode reader 31, and reference numeral 74 indicates a readout face capable of reading the barcodes 72 and 73. Another readout face 74 is provided on the reverse side of the barcode reader 31 so that it can read the barcodes 72 and 73 arranged to face the cavity section 61 at once by moving the cavity section 61 in the X axis direction. In the sections of the cavity section 61 where the containers 56 are held, notches are formed so that the barcodes 73 are arranged in the wall of the cavity section 61. Furthermore, the tags 71 are provided with holes having a size through which the top of the container 55 can enter, and a catch such as a projection or depression to prevent the tag 71 from moving around the periphery of the container 55.

The large capacity dispensing device 24 according to the present embodiment further comprises; a control section which controls the issuing of operating instructions and monitoring of the various operations for the suction and discharge mechanism 25, the Y axis carriage 27, the X axis carriage 50, the Z axis elevation mechanism, the magnetic section 32 having the magnetic blocks 62, the backlight section, the CCD camera 53, the support frame 51, and the barcode reader 31, according to instructions from an external source; an input section which inputs data and issues operation instructions to the control section; and an output section which outputs the results of monitoring the various operation instructions. In addition, the large capacity dispensing device 24 comprises a monitoring section which determines the state of the dispensing cylinders 10 based on the measurement results of the CCD camera 53, and acquires monitoring results which tie the results of this determination to each dispensing cylinder 10 and the operating instructions.

The monitoring section further comprises; a placement data storage section which stores placement data obtained from the placement confirmation section, a measurement results determination section which ties the measurement results in the form of the determination result of comparison with a standard optical pattern based on previously obtained data or experimentation, to the relevant operating instructions and data relating to the dispensing cylinder 10, and a monitoring results storage section which stores these monitoring results.

Here, the control section is configured by an information processing device, not shown in the diagram, having a CPU, various memory, and various program data. In addition, the input section is formed by, for example, a keyboard, mouse, switch or communication line and the like, which are not shown in the diagram. Furthermore, the output section may include a display section such as a liquid crystal or CRT, a printer, a CD drive, a DVD drive, a communication line or the like.

Figure 7:
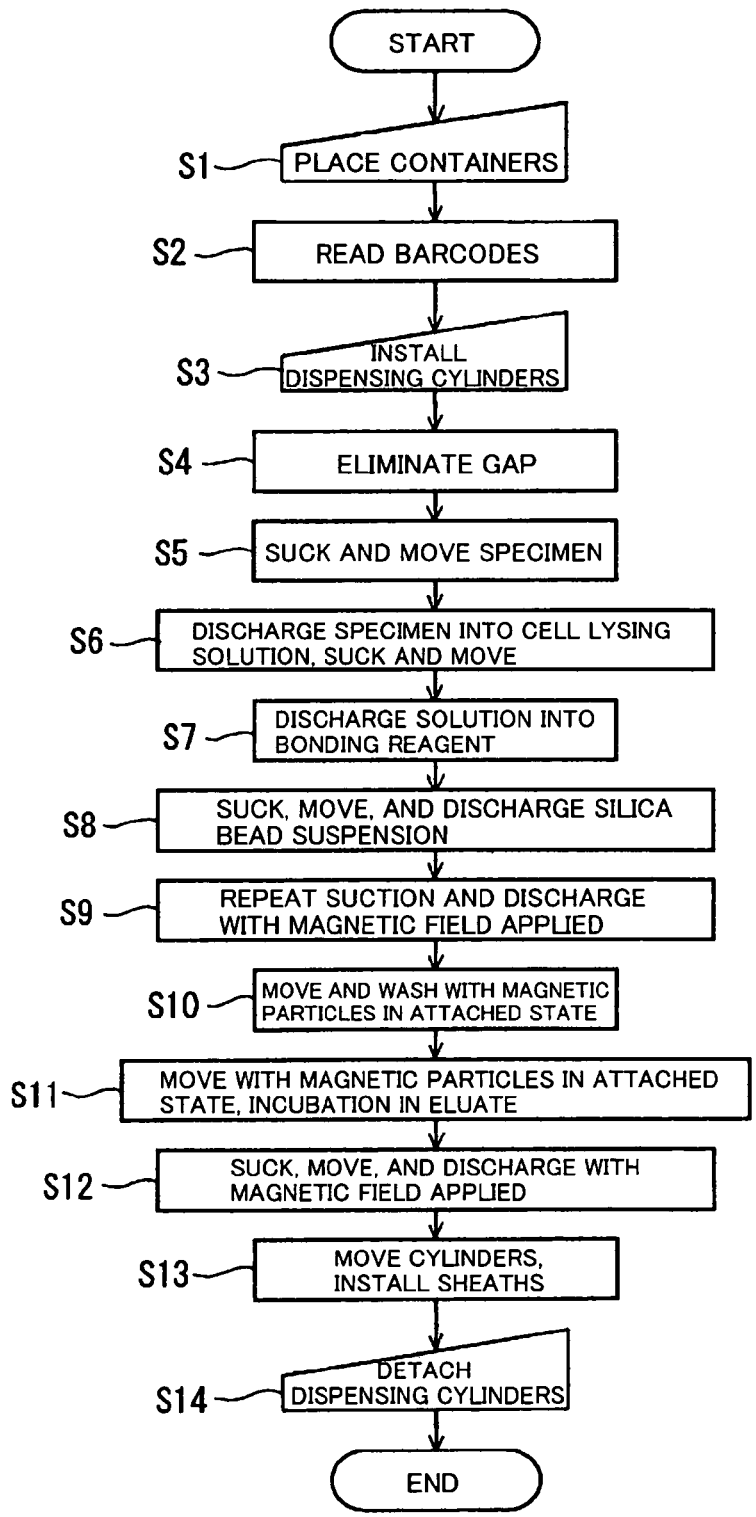
FIG. 7 is a flowchart of processing according to an embodiment of the present invention.

The following is a description of the operation of the present embodiment based on FIG. 7, using the example of a process where substances such as DNA, RNA and mRNA (referred to below as "DNA and the like") are collectively extracted from within the blood of respective human subjects. To perform this task, first a large volume of blood (for example 10 milliliters, 7 milliliters, 5 milliliters) must be collected using a vacuum blood tube.

In step S1, the whole blood collected from the respective humans is placed in the eight containers 56 to serve as the specimens, the sheaths 21 are placed in the eight containers 57, a dissolving solution for dissolving the cells in the blood is placed in each of the eight relatively large containers 58 of the first row, a binding reagent required to bind the DNA or the like to the magnetic silica beads as magnetic particles, for example a neutral buffer fluid, is placed in each of the eight containers of the second row, and wash liquid is placed in each of the eight containers of the third row. Furthermore, the relatively small capacity containers 59 are placed in the container placement stage 29 with a suspension of magnetic silica beads in each of the eight of the first row, and eluate such as pure water in each of the eight of the second row.

In step S2, after the containers are placed, the Y axis carriage 27 is moved in the Y axis direction until positioned in the cavity section 61, after which the motor 52 is driven to lower the support frame 51 and insert the barcode reader 31 into the cavity section 61. Then, by moving the X axis carriage 50, the barcode reader 31 sequentially reads the eight pairs of barcodes on the containers 55 and 56 while moving in the X axis direction, to confirm whether or not the containers 55 and 56 hold the intended contents or are scheduled to hold the intended contents. The comparison results may be displayed immediately on a display section serving as the output section, or may be stored in memory.

In step S3, the dispensing cylinders 10 are installed in the large capacity dispensing device 24. Installation of the dispensing cylinders 10 is performed manually by the operator. The dispensing cylinders 10 are installed so that the T shaped end sections 15 at the top of the rods 14 of the dispensing cylinders 10 engage with the T-shaped cavities 33 using the gap provided at the upper plate 34, and the sandwiching members 35 clamp the flange tubes 17 of the dispensing cylinders 10 from both sides while the guide section 36 guides the outer peripheral surface of the large diameter sections 12 of the dispensing cylinders 10.

In step S4, in order to eliminate the gap above the T shaped end sections 15 of the dispensing cylinders 10 which are installed and held in the T-shaped cavities 33 by frictional force, the gap elimination plate 37*a* is inserted into the gap by sliding inside the gap in the Y axis direction, thereby eliminating the gap.

In step S5, the Y axis carriage 27 provided with the eight dispensing cylinders 10 arranged in the X axis direction therein is shifted together with the dispensing cylinders 10 along the Y axis direction until reaching the row position of the containers 56, the Z axis elevation motor 46 is driven, the eight dispensing cylinders 10 are lowered together into the containers 56, the suction and discharge mechanism 25 is driven, the eight pistons 13 are moved upward together, and the blood of the respective patients as specimens stored in the containers 56 is sucked collectively into the respective large diameter sections 12 of the eight dispensing cylinders 10.

After suction, light is irradiated onto the large diameter sections 12 of the dispensing cylinders 10 by the backlight sections (not shown), and an image of the large diameter section 12 of the dispensing cylinder 10 is taken using the CCD camera 53 and the mirror 54. The CCD camera 53 can sequentially capture images of the eight dispensing cylinders 10 and confirm the presence or absence and volume of the specimen liquid sucked into the large diameter section 12, while being moved in the X axis direction by means of the X axis carriage 50.

In step S6, the dispensing cylinders 10 are moved in the Y axis direction until reaching the position of the first row of the containers 58, and the sucked blood is discharged into the cell lysing solution inside the containers 58. By stirring the cell lysing solution with the blood, the cells in the blood are lysed, and the DNA or the like is extracted into the liquid. The entire volume of the resulting solution is then sucked into the dispensing cylinders 10, and the dispensing cylinders 10 are moved in the Y axis direction.

In step S7, the dispensing cylinders 10 are moved to the position of the second row of the containers 58, and the solution is discharged into the bonding reagent which facilitates bonding of the DNA and the like with the magnetic particles. When the magnetic particles are silica beads, for example, the bonding reagent is a neutral buffer solution.

In step S8, the empty dispensing cylinders 10, having discharged the solution, are moved in the Y axis direction until reaching the first row of the containers 59, to suck the magnetic silica bead suspension, and the dispensing cylinders 10 are then moved in the Y axis direction until reaching the second row of the containers 58, where the suspension is discharged into the containers 58 and mixed together with the solution.

In step S9, the small diameter sections 11 of the dispensing cylinders 10 are raised into the magnetic activity region of the magnetic section 32. When the small diameter sections 11 reach this region, in order to exert a magnetic field on the small diameter sections 11, the motor 63 is driven to move the eight magnetic blocks 62 near to the eight small diameter sections 11. With the magnetic blocks 62 near the small diameter sections 11, suction and discharge of the solution is repeated. The silica beads to which the DNA or the like has adhered, are attached onto the inside wall of the small diameter section 11 and are thus isolated, and the residual fluid is discharged.

In step S10, in this state in which the magnetic blocks 62 are near the small diameter sections 11, the dispensing cylinders 10 are moved in the Y axis direction, with the silica beads with which the DNA or the like has bonded remaining attached to the inside wall of the small diameter sections 11 of the dispensing cylinders 10, and repositioned at the third row of the containers 58 which contain the wash liquid. The small diameter sections 11 are inserted into the containers 58, and the isolated silica beads are resuspended by repeating suction and discharge of the wash liquid with the magnetic blocks 62 moved away from the small diameter sections 11 and the magnetic field removed. After suction and discharge is performed for a predetermined number of times, the magnetic blocks 62 are again brought near the small diameter sections 11, suction and discharge is repeated causing the silica beads to again attach onto the inside wall of the small diameter sections 11, and the residual fluid is discharged.

In step S11, the dispensing cylinders 10 are moved to the position of the second row of the containers 59 which contain the eluate for separating the DNA or the like from the silica beads, and the solution is sucked and the dispensing cylinders 10 are moved in the Y axis direction. Then with the magnetic blocks 62 moved away, the solution is discharged together with the silica beads into the containers 60 where the heating block is provided, and incubation is performed.

In step S12, after a predetermined length of time has passed, with the magnetic blocks 62 near the small diameter sections 11, the entire volume of the solution is sucked, the dispensing cylinders 10 are moved in the Y axis direction until reaching the containers 55, and the solution is discharged. In this manner, the silica beads remain attached onto the inside wall of the small diameter sections 11, and a solution in which the DNA or the like is suspended is obtained as the residual solution.

After the processing is completed, in step S13 the dispensing cylinders 10 are moved to the containers 57 which hold the sheaths 21, and by lowering the small diameter sections 11, the sheaths 21 engage with the outer ring sections 23, thereby fitting the sheaths 21 to the small diameter sections 11.

In step S14, the operator detaches the dispensing cylinder 10 from the large capacity dispensing device 24 by grasping the sheath 21, and the dispensing cylinder 10 is disposed of.

In this manner, it is possible to remove the dispensing cylinders 10 without any reagents or the like adhering to the hand of the operator, which is safe because the operator is free from contamination of the reagents or specimens. In each of step S3, step S5, step S6, step S7, step S10 and step S12, preferably images of the state of each dispensing cylinder 10 are taken by the CCD camera 53, to confirm the operation thereof after processing is completed. This allows highly reliable processing to be performed.

Figure 8:
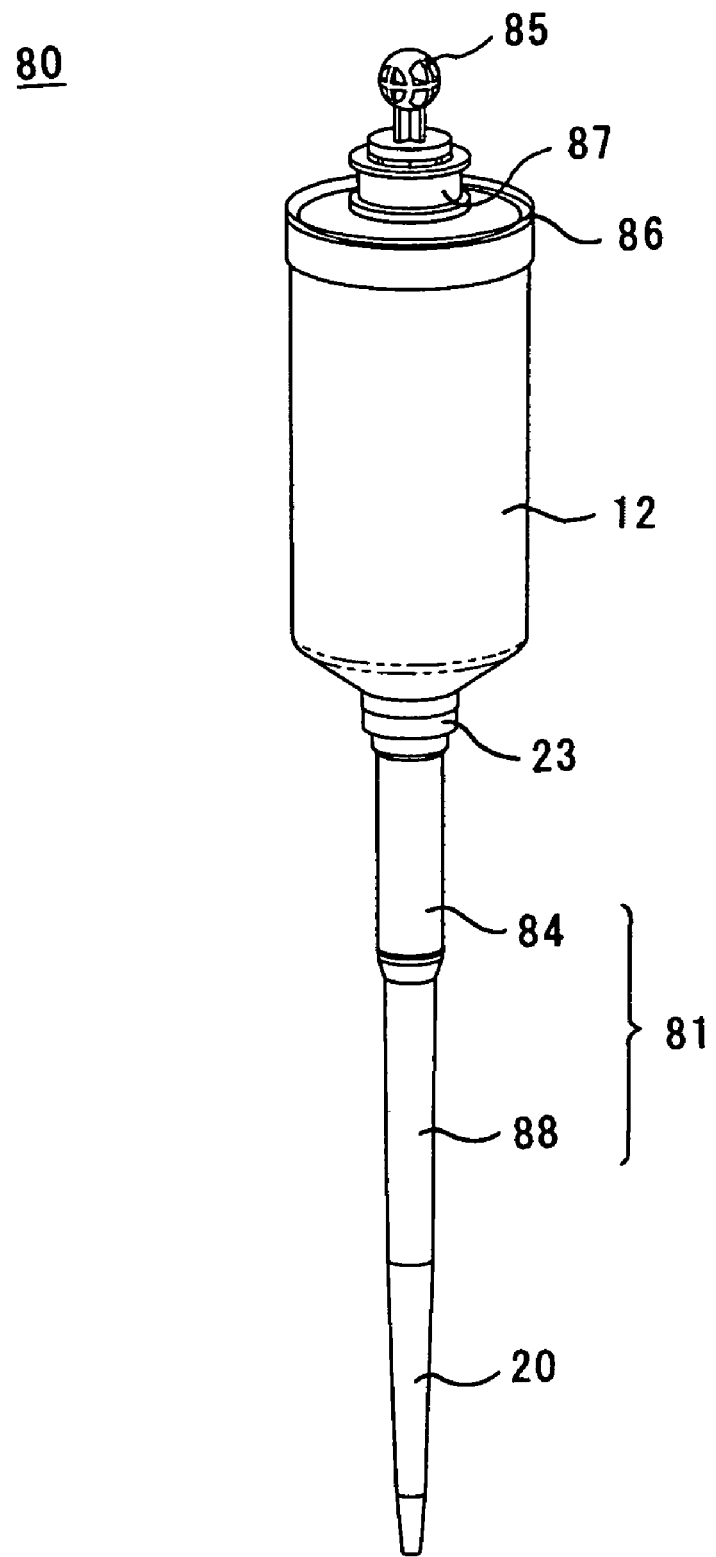
FIG. 8 is a diagram showing a dispensing cylinder according to another embodiment of the present invention.

FIG. 8 shows a dispensing cylinder 80 used in a large capacity dispensing device (indicated by reference numeral 124 in FIG. 9) according to another embodiment. In the following description, those components which are the same as those in FIG. 1 to FIG. 6 are labeled with the same reference numerals, and description thereof is omitted. The dispensing cylinder 80 comprises: a tapered approximately cylindrical small diameter section 81; an approximately cylindrical large diameter section 12 which communicates with the small diameter section 81 and is capable of holding fluid; a disk shaped piston (not shown) slidably provided within the large diameter section 12 and corresponding to the sliding section which enables fluid to be sucked to and discharged from the large diameter section 12 through the small diameter section 81; a rod (not shown) provided with one end secured to the piston; and a ball end section 85 formed in an approximate ball shape at the other end of the rod outside the large diameter section 12, as the connection section which connects the piston in a detachable manner to the actuating part of the suction and discharge mechanism which drives the piston. Accordingly, the large capacity dispensing device according to the present embodiment (reference numeral 124 in FIG. 9) differs from the large capacity dispensing device 24, in that cylindrical slots which are approximately round when viewed front on are provided as eight connection target sections that engage the ball end sections 85 to be connected with the ball end sections 85 by frictional force.

In the present embodiment, the small diameter section 81 comprises an upper small diameter section 84 and a lower small diameter section 88, wherein the diameter of the upper small diameter section 84 is significantly smaller than that of the large diameter section 12, but relatively larger than that of the lower small diameter section 88. Consequently, a sufficient magnetic field can be exerted inside the upper small diameter section 84, and even when the magnetic particles are attached onto the inside wall of the upper small diameter section 84, the attached magnetic particles do not impede the flow of the fluid. Reference numeral 86 indicates a head, and reference numeral 87 indicates a flange tube 87.

Figure 9:
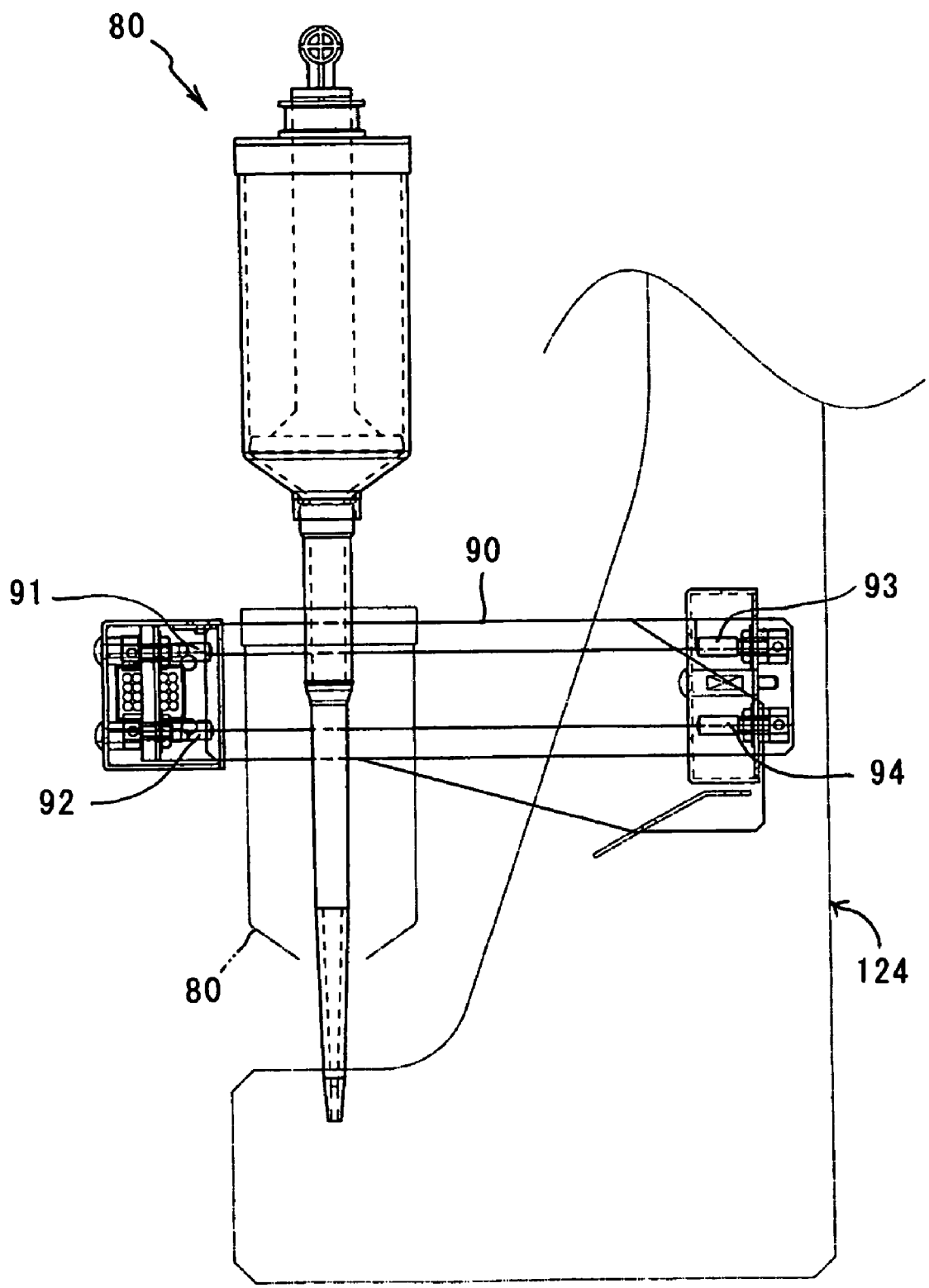
FIG. 9 is a diagram showing a large capacity dispensing device according to another embodiment of the present invention which has an optical measuring section.

FIG. 9 shows the fluid volume detection mechanism in the large capacity dispensing device 124. In the large capacity dispensing device 124 according to the present embodiment, instead of providing the X axis carriage 50 capable of moving along the X axis direction and the CCD camera 53 and the mirror 54 provided on the X axis carriage 50, a pair of a light emitting element 91 and a light receiving element 93, and a pair of light emitting element 92 and a light receiving element 94 are provided for each of the group of eight dispensing cylinders 80, secured to a support plate 90 perpendicularly to the axial direction so as to be on either side of each dispensing cylinder 80. In this case, threshold values are respectively set for the level of electric signal output from the light receiving elements so that one of the pairs detects the presence or absence of fluid inside the large diameter section 12, and the other pair detects the presence or absence of fluid inside the small diameter section 81. The fluid volume is measured by measuring the presence or absence of fluid in the large diameter section and the small diameter section while moving the dispensing cylinder 80 vertically. In the present embodiment, there is no need to provide a movement mechanism for the CCD camera, mirror, backlight and X axis carriage, which allows the scale of the device to be suppressed, and manufacturing costs to be reduced.

Figure 10:
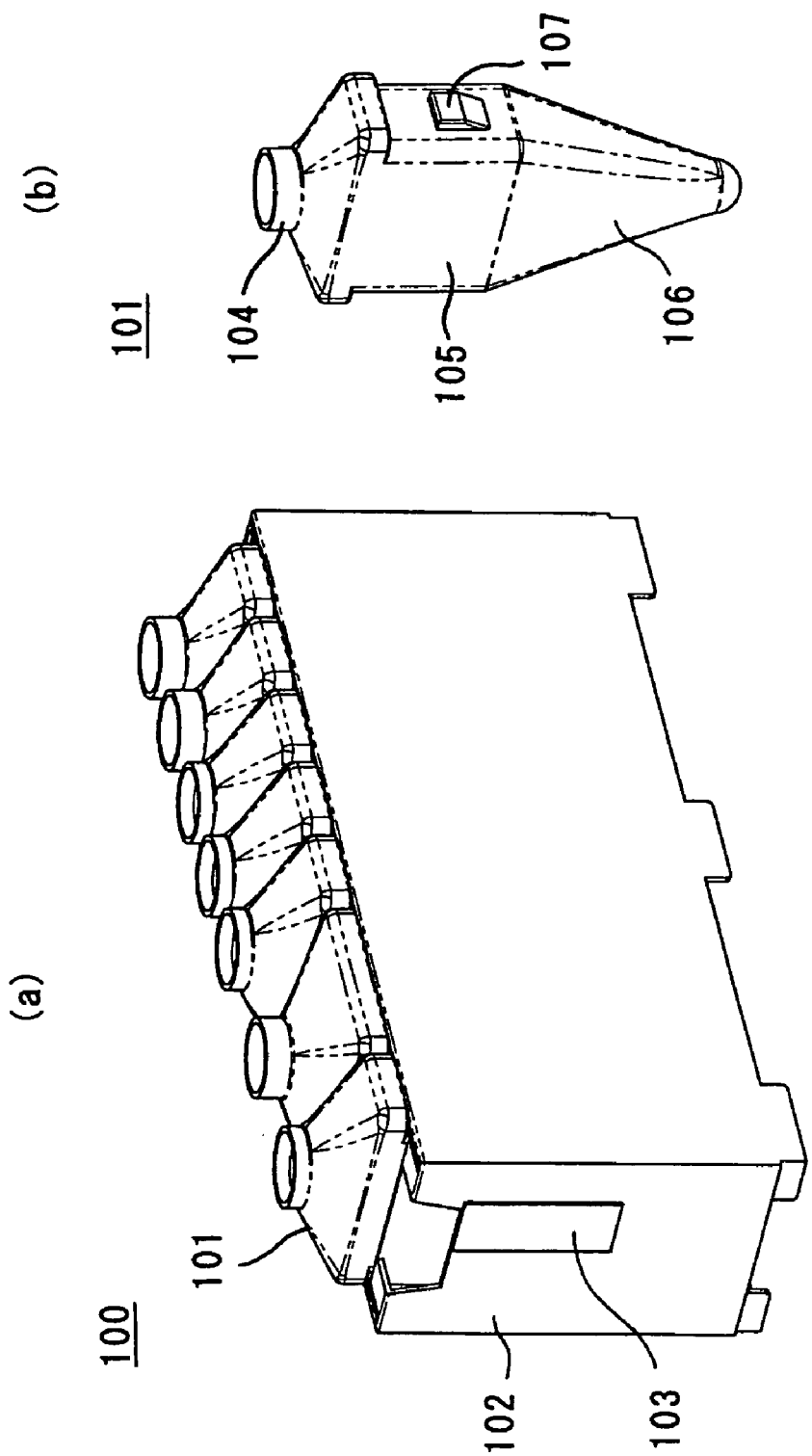
FIG. 10 is a perspective view showing a multiple container storage section according to an embodiment of the present invention.

FIG. 10 (*a*) shows a multiple container storage section 100 used in the large capacity dispensing device 124 according to the present embodiment. The multiple container storage section 100 comprises bottles 101 as the multiple containers (in this case seven) which hold or are capable of holding various reagents, and a box 102 which stores the bottles 101 in a row. A barcode 103 as an identifier displaying information relating to the multiple container storage section 100, for example the expiration date, the type of reagent, the type of specimen, the identification number, and the person in charge, is affixed to the side face of the bottle 101 in the box 102.

FIG. 10 (*b*) shows one example of a bottle 101, although the box 102 may contain bottles of many different capacities. The bottle 101 has a neck 104, a body 105 and a tapered base 106, and a catch 107 provided on the body 105 which prevents juddering of the bottle 101 within the box 102.

Figure 11:
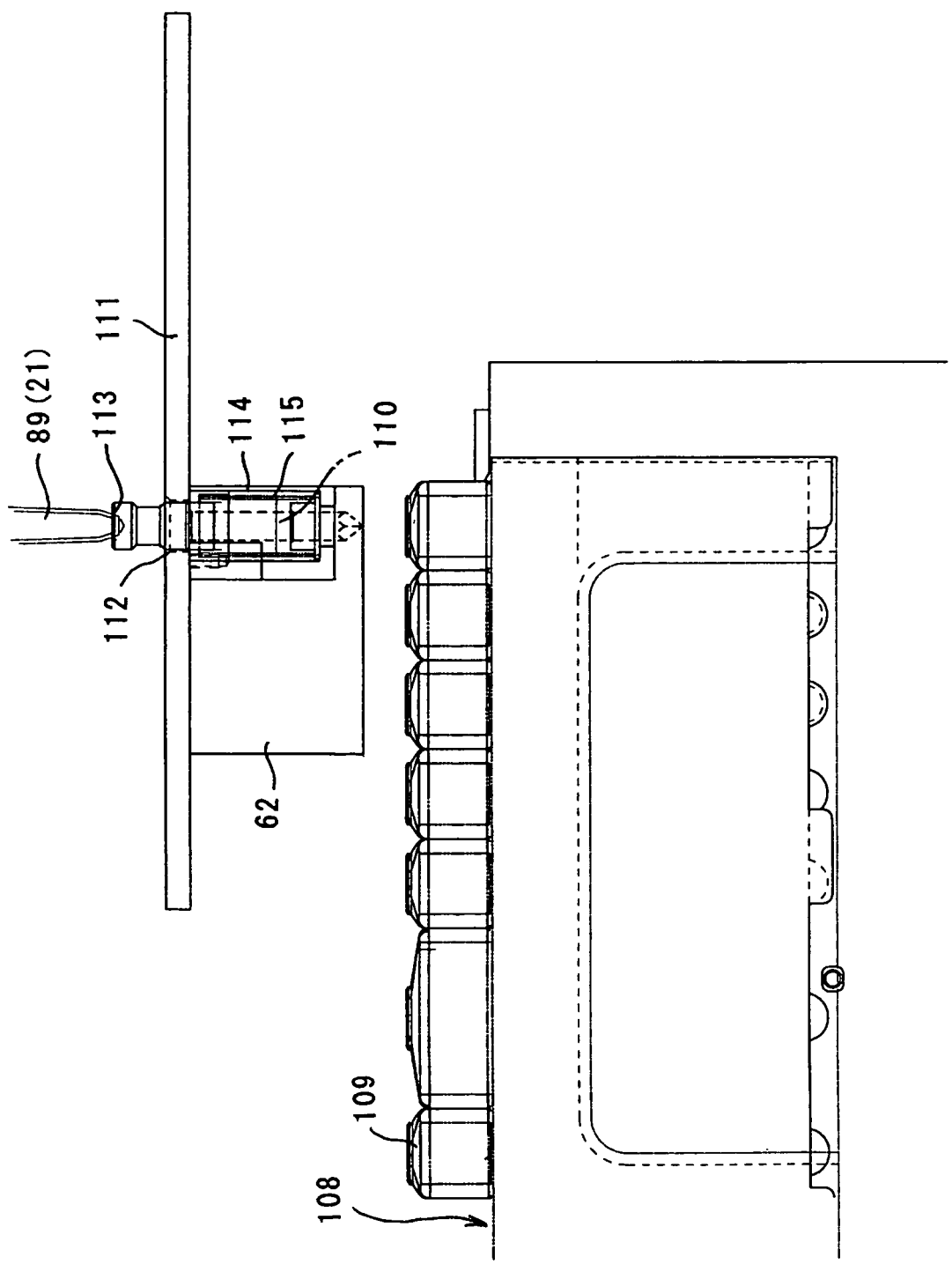
FIG. 11 is a diagram showing a perforating mechanism according to an embodiment of the present invention.

FIG. 11 shows the perforating mechanism provided in the large capacity dispensing device 124.

The perforating mechanism is used when the openings of the bottles 109 in the multiple container storage section 108 are previously sealed with perforable lids. The perforating mechanism comprises: a through hole 112 formed in a position behind the magnetic block 62 in a plate 111 to which the magnetic blocks 62 are mounted, and which is movably provided so that the magnetic blocks 62 comes closer towards or away from the dispensing cylinder 80; a perforating pin 110 which passes through the through hole 112 and extends below the plate 111; a top end section 113 of the perforating pin 110 having a depression which receives the tip of the sheath 21 when the sheath 21 is fitted to the dispensing cylinder 80; a pipe 114 which protrudes below the plate 111 and surrounds the through hole 112; and a spring 115 having one end attached to the pipe 114 and the other end attached to the perforating pin 110, to elastically urge the perforating pin 110 upward. To perforate the lid of the bottle 109 using the perforating mechanism, first the plate 111 is moved so that the top end section 113 of the perforating pin 110 is positioned directly beneath a tip 89 of the dispensing cylinder 80. Next the dispensing cylinder 80 is moved downward in the Z axis direction, and with the top end section 113 and the tip of the sheath 21 in contact, the dispensing cylinder 10 is moved downward and the lid of the bottle 190 is perforated. When the perforation is completed, the dispensing cylinder 80 is moved upward and the tip of the sheath 21 is separated from the top end section 113, so that the perforating pin 110 is positioned above the bottle 109.

Figure 12:
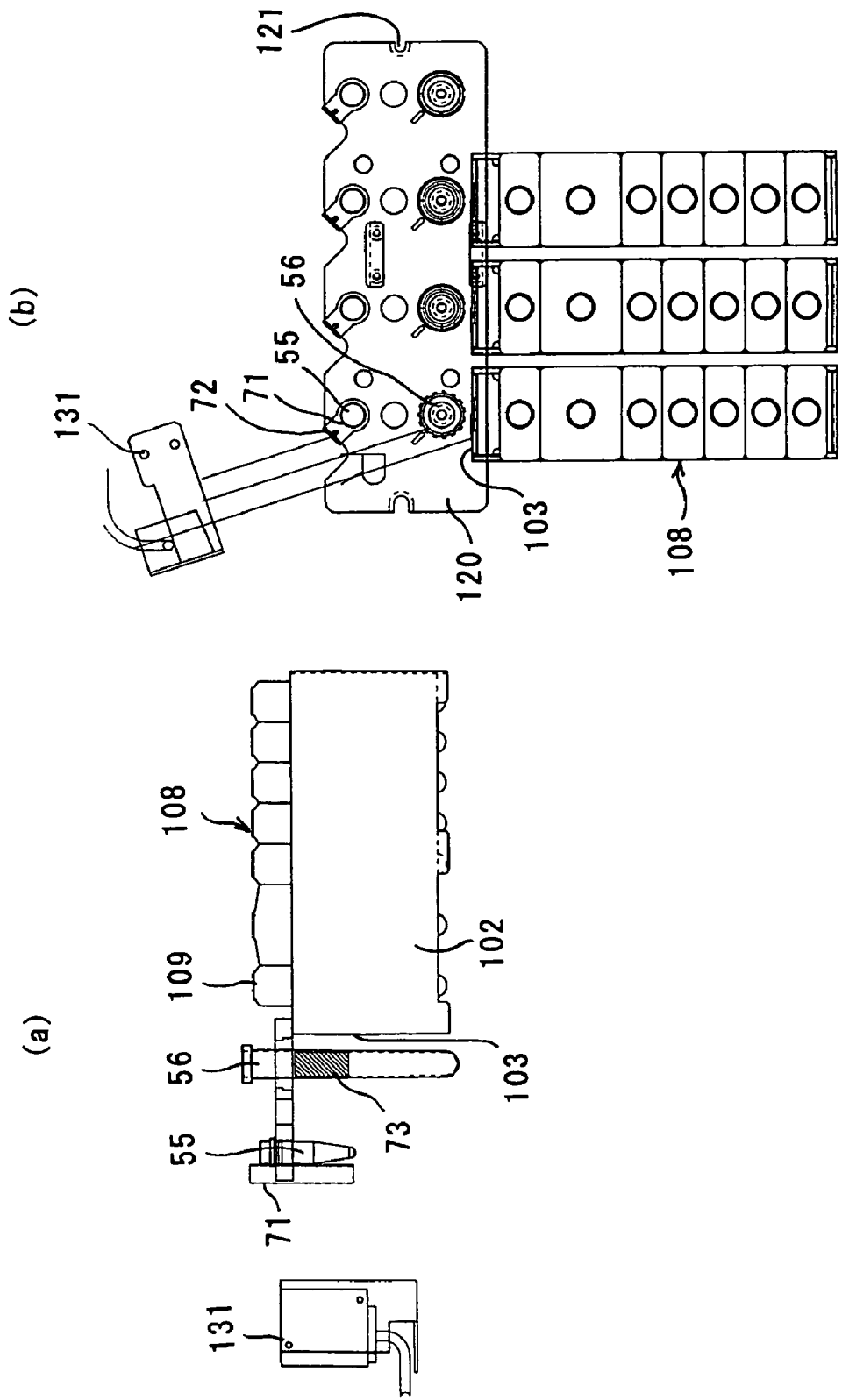
FIG. 12 is an illustrative drawing relating to a barcode reader according to another embodiment of the present invention.

FIG. 12 describes a barcode reader 131, serving as the readout section, in the large capacity dispensing device 124. FIG. 12 (*a*) is a side view showing the barcode reader 131, and the group of containers to which the barcodes to be read by the barcode reader 131 are attached, and FIG. 12 (*b*) is a plan view of the barcode reader 131 and the group of containers. In the large capacity dispensing device 124 according to the present embodiment, there is no mechanism provided for moving the barcode reader in the X axis direction together with the CCD camera and the mirror. Instead, a mechanism which moves the barcode reader 131 in the X axis direction is provided in the space corresponding to the cavity section 61.

As shown in FIG. 12 (*b*), the barcode reader 131 can read the barcodes 72, 73 and 103 respectively attached to the containers 55 and 56 and the multiple container storage section 108, without omission, by the readout face thereof moving in parallel in the X axis direction while adopting a predetermined angle relative to the direction of arrangement of the containers.

Here, reference numeral 120 indicates the mounting plate for mounting the containers 55 and 56 and the multiple container storage section 108, and reference numeral 121 indicates a connecting hole used to connect the mounting plate 120. These groups of containers are placed in the part of the large capacity dispensing device 124 that corresponds to the container placement stage 29 of the large capacity dispensing device 24.

In the large capacity dispensing device according to the embodiment shown in FIG. 8 through FIG. 12, the reading of the barcodes by the barcode reader 131 described in step S2 above can be performed by simply moving the barcode reader 131 in the X axis direction, because the barcode reader 131 is already inside the space corresponding to the cavity section 61, and there is no need for the step where the Y axis carriage 27 is moved in the Y axis direction and inserted into the cavity section 61. Furthermore, the detection of the fluid volume in step S5 does not require the step in which irradiation by the backlight and imaging by the CCD camera 53 and mirror 54 are performed, nor the step in which the CCD camera 53 is moved in the X axis direction, and the presence or absence of fluid and the volume of fluid can be detected by detecting the presence or absence of fluid in each large diameter section 12 and small diameter section 81 using the two pairs of light emitting elements 91 and 92 and light receiving elements 93 and 94 for each dispensing cylinder 80.

The embodiments described above are described in concrete terms to allow better understanding of the present invention, and should not be construed as limiting. Accordingly, any modification thereof may be made within the scope of the purport of the invention. For example, the quantity, size and shape of the various components used in the embodiments above are not restricted to those described. For example, the number of containers and dispensing cylinders is not limited to eight or eight rows, and may be any other number including one or one row of containers and dispensing cylinders.

Furthermore, the arrangement of the dispensing cylinders is not limited to a line, and the dispensing cylinders may be arranged in a matrix or ring shape. Furthermore, the arrangement of the containers can also be changed according to the arrangement and quantity of the dispensing cylinders. The capacity of the dispensing cylinders and the containers is not limited to 50 milliliters. The shape of the sliding section is not limited to that described in the embodiments.

Furthermore, in the description above, the process of extracting DNA or the like from blood was described, but the present invention is not limited to this processing or the processing procedure described. In addition to this processing, the present invention can be applied to various other biochemical processing such as the extraction of proteins such as antigens and antibodies, the extraction of plasmids and DNA and the like from the tissue of organisms such as humans, and the extraction or concentration of DNA and the like, bacteria, viruses, and proteins from foodstuffs (such as beverages, solids, meat vegetables) and the production of large volumes of solution from small volumes of specimen.

Furthermore, the configuration of the connection section of the dispensing cylinder, that is the T shaped end section or ball end section, is not limited to connection to a T shaped or circular cavity provided as the connection target in the plate, and it is possible to provide a connection with components of various other shapes. Furthermore, the shape of the engagement section is not limited to the outer ring shape, and may be a square post, for example. Furthermore, a slanted face may be formed at the bottom end of the outer ring section 23 to enable insertion into the sheath to be achieved more easily.

Furthermore, the constituent elements, components and devices described above, for example the dispensing cylinders, the sliding section, the large capacity dispensing device, the suction and discharging mechanism, the optical measuring section, the magnetic section, the Y axis carriage, the X axis carriage, the fitting section, the securing section, the connection section, and the reading section, may be combined at will with the appropriate modifications.

- 10, 80 . . . Dispensing cylinder
- 11, 81 . . . Small diameter section
- 12 . . . Large diameter section
- 13 . . . Piston (sliding section)
- 14 . . . Rod (sliding section)
- 15 . . . T shaped end section (connection section)
- 17 . . . Flange tube (securing section)
- 21 . . . Sheath
- 23 . . . Engagement section
- 24, 124 . . . Large capacity dispensing device
- 25 . . . Suction and discharge mechanism
- 26 . . . Main body section
- 27 . . . Y axis carriage
- 29 . . . Container placement stage
- 30 . . . Optical measurement section
- 31, 131 . . . Barcode reader
- 32 . . . Magnetic section
- 33 . . . T-shaped cavity (connection target section)
- 35 . . . Sandwiching member (fitting section)
- 37*a* . . . Gap elimination plate (gap elimination mechanism)
- 50 . . . X axis carriage
- 53 . . . CCD camera (optical measuring section)
- 54 . . . Mirror (optical measuring section)
- 55, 56, 57, 58, 59, 60, 101, 109 . . . Container (bottle)
- 85 . . . Ball end section (connection section)
- 100, 108 . . . Multiple container storage section

The invention claimed is:

1. A large capacity dispensing device, comprising:
one or more dispensing cylinders, each of the dispensing cylinders comprising:
a small diameter section,
a large diameter section which communicates with said small diameter section and is capable of holding fluids,
a sliding section provided in a slidable manner within said large diameter section which enables fluid to be sucked and discharged to and from said large diameter section through said small diameter section, and
a connection section connected to the sliding section so that the sliding section is axially positioned between the connection section and the small diameter section;
a suction and discharge mechanism, the suction and discharge mechanism comprising:
an actuating part which connects to each of said connection sections in a detachable manner and drives said sliding sections, and
a non-actuating part comprising one or more fitting sections, each of which fits a respective one of said large diameter sections in a detachable manner to said suction and discharge mechanism to secure said respective large diameter section to said suction and discharge mechanism;
a container placement area in which a plurality of containers can be placed; and
a movement section which enables said one or more dispensing cylinders to move relative to said container placement area;
wherein the sliding section comprises:
a disk-shaped piston which slides inside the large diameter section;
a rod, one end of which is secured to the piston, wherein the connection section is provided at the other end of the rod; and
a tube supported by an end of the large diameter section that axially opposes the small diameter section, the tube having a diameter and being positioned, relative to the rod, such that:
the rod passes through the inside of the tube,
relative axial movement between the rod and the tube is permitted,
the rod is substantially axially aligned with the large diameter section at the end of the large diameter section that axially opposes the small diameter section, and
the tube is axially positioned between the piston and the connection section and thereby prevents the piston from exiting the large diameter section through the end of the large diameter section that axially opposes the small diameter section.

2. A large capacity dispensing device according to claim 1, comprising a gap elimination mechanism which eliminates a gap between said connection section of said dispensing cylinder, and a connection target section provided on said suction and discharge mechanism which connects to said connection section.

3. A large capacity dispensing device according to claim 1, wherein said small diameter section of said dispensing cylinder comprises an engagement section formed so as to protrude outward from said small diameter section, and said container placement area contains in addition to a plurality of containers, one or more sheaths which can be fitted by engaging an opening thereof with said engagement section so that the sheath covers said small diameter section of said dispensing cylinder, arranged in a manner that enables fitting to said small diameter section.

4. A large capacity dispensing device according to claim 1, wherein a magnetic section capable of exerting and removing a magnetic field into the small diameter section of said dispensing cylinder, is provided at a predetermined position in the vicinity of a path of vertical movement of said small diameter section.

5. A large capacity dispensing device according to claim 1, comprising an optical measuring section capable of optically measuring a fluid level in said dispensing cylinder.

6. A large capacity dispensing device according to claim 1, wherein an identifier is affixed to a container placed in said container placement area which identifies said container, and which comprises a readout section which reads the identifier affixed to said container.

7. A large capacity dispensing device according to claim 1, wherein said container placement area comprises a temperature adjustment section which adjusts the temperature of containers placed in the area.

8. A large capacity dispensing device, comprising:
one or more dispensing cylinders, each of the dispensing cylinders comprising:
a small diameter section,
a large diameter section which communicates with said small diameter section and is capable of holding fluids,
a sliding section provided in a slidable manner within said large diameter section which enables fluid to be sucked and discharged to and from said large diameter section through said small diameter section, and
a connection section connected to the sliding section so that the sliding section is axially positioned between the connection section and the small diameter section;
a suction and discharge mechanism, the suction and discharge mechanism comprising:
an actuating part which connects to each of said connection sections in a detachable manner and drives said sliding sections, and
a non-actuating part comprising one or more fitting sections, each of which fits a respective one of said large diameter sections in a detachable manner to said suction and discharge mechanism to secure said respective large diameter section to said suction and discharge mechanism;
a container placement area in which a plurality of containers can be placed; and
a movement section which enables said one or more dispensing cylinders to move relative to said container placement area;
wherein the sliding section comprises a tube supported by an end of the large diameter section that axially opposes the small diameter section, the tube comprising a flange; and
wherein the fitting section comprises a cylindrical sandwiching member that is axially positioned between the flange of the tube and the end of the large diameter section that axially opposes the small diameter section, the cylindrical sandwiching member clamping the tube in an elastically energized state.

9. A large capacity dispensing device according to claim 8, comprising a gap elimination mechanism which eliminates a gap between said connection section of said dispensing cylinder, and a connection target section provided on said suction and discharge mechanism which connects to said connection section.

10. A large capacity dispensing device according to claim 8, wherein said small diameter section of said dispensing cylinder comprises an engagement section formed so as to protrude outward from said small diameter section, and said container placement area contains in addition to a plurality of containers, one or more sheaths which can be fitted by engaging an opening thereof with said engagement section so that the sheath covers said small diameter section of said dispensing cylinder, arranged in a manner that enables fitting to said small diameter section.

11. A large capacity dispensing device according to claim 8, wherein a magnetic section capable of exerting and removing a magnetic field into the small diameter section of said dispensing cylinder, is provided at a predetermined position in the vicinity of a path of vertical movement of said small diameter section.

12. A large capacity dispensing device according to claim 8, comprising an optical measuring section capable of optically measuring a fluid level in said dispensing cylinder.

13. A large capacity dispensing device according to claim 8, wherein an identifier is affixed to a container placed in said container placement area which identifies said container, and which comprises a readout section which reads the identifier affixed to said container.

14. A large capacity dispensing device according to claim 8, wherein said container placement area comprises a temperature adjustment section which adjusts the temperature of containers placed in the area.

15. A method of using a large capacity dispensing device, comprising:
a suction and discharge step for sucking or discharging a predetermined fluid to or from a container by using:
the container placed in a container placement area;
one or more dispensing cylinders, each of the dispensing cylinders comprising: a small diameter section, a large diameter section which communicates with said small diameter section and is capable of holding fluid, a sliding section provided in a slidable manner within said large diameter section which enables fluid to be sucked and discharged to and from said large diameter section through said small diameter section, and a connection section connected to the sliding section so that the sliding section is axially positioned between the connection section and the small diameter section; and
a suction and discharge mechanism, the suction and discharge mechanism comprising: an actuating part which connects to each of said connection sections in a detachable manner and drives said sliding sections, and a non-actuating part comprising one or more fitting sections, each of which fits a respective one of said large diameter sections in a detachable manner to said suction and discharge mechanism to secure said respective large diameter section to said suction and discharge mechanism;
and
a movement step for moving said one or more dispensing cylinders relative to said container placement area;
wherein the sliding section comprises:
a disk-shaped piston which slides inside the large diameter section;
a rod, one end of which is secured to the piston, wherein the connection section is provided at the other end of the rod; and
a tube supported by an end of the large diameter section that axially opposes the small diameter section, the tube having a diameter and being positioned, relative to the rod, such that:
the rod passes through the inside of the tube,
relative axial movement between the rod and the tube is permitted, the rod is substantially axially aligned with the large diameter section at the end of the large diameter section that axially opposes the small diameter section, and the tube is axially positioned between the piston and the connection section and thereby prevents the piston from exiting the large diameter section through the end of the large diameter section that axially opposes the small diameter section.

16. A method of using a large capacity dispensing device according to claim 15, comprising a sheath fitting step for moving said dispensing cylinder to a position in said container placement area where said sheath is placed, and fitting said sheath by lowering said dispensing cylinder so that said sheath covers said small diameter section of said dispensing cylinder.

17. A method of using a large capacity dispensing device according to claim 15, comprising an operation checking step for, during said suction and discharge step, checking the result of suction or discharge, by optically measuring a fluid volume within said dispensing cylinder.

18. A method of using a large capacity dispensing device according to claim 15, comprising a container placement checking step for checking the placement of a container in said container placement area, by reading an identifier of a container placed in the area.

19. A method of using a large capacity dispensing device according to claim 15, comprising a step for adjusting the temperature of a fluid by using said dispensing cylinder to transfer a fluid to a container where a temperature adjustment section which adjusts the temperature of said container is provided.

20. A method of using a large capacity dispensing device according to claim 15, comprising a gap removal step for eliminating a gap between a connection section of said dispensing cylinder and a connection target section provided on said suction and discharge mechanism which connects to said connection section.

21. A method of using a large capacity dispensing device according to claim 15 comprising; a step for moving a small diameter section of a dispensing cylinder vertically to a magnetic activity region provided in a path of vertical movement of said small diameter section, and a step for exerting a magnetic field into or removing a magnetic field from said small diameter section in said magnetic activity region when a solution in which magnetic particles are suspended is sucked or discharged using a dispensing cylinder.

22. A method of using a large capacity dispensing device, comprising:
  a suction and discharge step for sucking or discharging a predetermined fluid to or from a container by using:
    the container placed in a container placement area;
    one or more dispensing cylinders, each of the dispensing cylinders comprising: a small diameter section, a large diameter section which communicates with said small diameter section and is capable of holding fluid, a sliding section provided in a slidable manner within said large diameter section which enables fluid to be sucked and discharged to and from said large diameter section through said small diameter section, and a connection section connected to the sliding section so that the sliding section is axially positioned between the connection section and the small diameter section; and
    a suction and discharge mechanism, the suction and discharge mechanism comprising: an actuating part which connects to each of said connection sections in a detachable manner and drives said sliding sections, and a non-actuating part comprising one or more fitting sections, each of which fits a respective one of said large diameter sections in a detachable manner to said suction and discharge mechanism to secure said respective large diameter section to said suction and discharge mechanism;
  and
  a movement step for moving said one or more dispensing cylinders relative to said container placement area;
  wherein the sliding section comprises a tube supported by an end of the large diameter section that axially opposes the small diameter section, the tube comprising a flange; and
  wherein the fitting section comprises a cylindrical sandwiching member that is axially positioned between the flange of the tube and the end of the large diameter section that axially opposes the small diameter section, the cylindrical sandwiching member clamping the tube in an elastically energized state.

23. A method of using a large capacity dispensing device according to claim 22, comprising a sheath fitting step for moving said dispensing cylinder to a position in said container placement area where said sheath is placed, and fitting said sheath by lowering said dispensing cylinder so that said sheath covers said small diameter section of said dispensing cylinder.

24. A method of using a large capacity dispensing device according to claim 22, comprising an operation checking step for, during said suction and discharge step, checking the result of suction or discharge, by optically measuring a fluid volume within said dispensing cylinder.

25. A method of using a large capacity dispensing device according to claim 22, comprising a container placement checking step for checking the placement of a container in said container placement area, by reading an identifier of a container placed in the area.

26. A method of using a large capacity dispensing device according to claim 22, comprising a step for adjusting the temperature of a fluid by using said dispensing cylinder to transfer a fluid to a container where a temperature adjustment section which adjusts the temperature of said container is provided.

27. A method of using a large capacity dispensing device according to claim 22, comprising a gap removal step for eliminating a gap between a connection section of said dispensing cylinder and a connection target section provided on said suction and discharge mechanism which connects to said connection section.

28. A method of using a large capacity dispensing device according to claim 22 comprising; a step for moving a small diameter section of a dispensing cylinder vertically to a magnetic activity region provided in a path of vertical movement of said small diameter section, and a step for exerting a magnetic field into or removing a magnetic field from said small diameter section in said magnetic activity region when a solution in which magnetic particles are suspended is sucked or discharged using a dispensing cylinder.

* * * * *